United States Patent
Bentley et al.

(10) Patent No.: US 8,034,825 B2
(45) Date of Patent: *Oct. 11, 2011

(54) CHEMICALLY MODIFIED SMALL MOLECULES

(75) Inventors: Michael D. Bentley, Huntsville, AL (US); Tacey X. Viegas, Madison, AL (US); Richard R. Goodin, Fayerville, TN (US); Lin Cheng, Huntsville, AL (US); Xuan Zhao, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/822,935

(22) Filed: Jun. 24, 2010

(65) Prior Publication Data

US 2010/0305147 A1 Dec. 2, 2010

Related U.S. Application Data

(63) Continuation of application No. 11/015,196, filed on Dec. 16, 2004, now Pat. No. 7,786,133.

(60) Provisional application No. 60/530,122, filed on Dec. 16, 2003.

(51) Int. Cl.
*A61K 31/485* (2006.01)
*C07D 489/08* (2006.01)

(52) U.S. Cl. .......................................... 514/282; 546/44

(58) Field of Classification Search .................. 514/282; 546/44
See application file for complete search history.

(56) References Cited

U.S. PATENT DOCUMENTS

| | | |
|---|---|---|
| 4,223,163 A | 9/1980 | Guilloty |
| 4,366,159 A | 12/1982 | Magruder |
| 4,489,079 A | 12/1984 | Giudice et al. |
| 4,587,046 A | 5/1986 | Goodman et al. |
| 4,670,417 A | 6/1987 | Iwasaki et al. |
| 4,719,215 A | 1/1988 | Goldberg |
| 4,730,048 A | 3/1988 | Portoghese |
| 4,801,575 A | 1/1989 | Pardridge |
| 4,806,556 A | 2/1989 | Portoghese |
| 4,861,781 A | 8/1989 | Goldberg |
| 5,053,228 A | 10/1991 | Mori et al. |
| 5,099,074 A | 3/1992 | Mueller et al. |
| 5,102,887 A | 4/1992 | Goldberg |
| 5,122,614 A | 6/1992 | Zalipsky |
| 5,130,126 A | 7/1992 | Koyama et al. |
| 5,159,081 A | 10/1992 | Cantrell et al. |

(Continued)

FOREIGN PATENT DOCUMENTS

DE 19632440 A1 2/1998

(Continued)

OTHER PUBLICATIONS

Asai et al., "Naloxone Inhibits Gastric Emptying in the Rat", Anesth. Analg., 1999, pp. 204-208, vol. 88.

(Continued)

*Primary Examiner* — Sharmila G. Landau
*Assistant Examiner* — Trevor Love
(74) *Attorney, Agent, or Firm* — Jones Day

(57) ABSTRACT

The invention provides small molecule drugs that are chemically modified by covalent attachment of a water-soluble oligomer obtained from a monodisperse or bimodal water-soluble oligomer composition. A conjugate of the invention, when administered by any of a number of administration routes, exhibits a reduced biological membrane crossing rate as compared to the biological membrane crossing rate of the small molecule drug not attached to the water-soluble oligomer.

17 Claims, 10 Drawing Sheets

U.S. PATENT DOCUMENTS

| | | | |
|---|---|---|---|
| 5,225,206 A | 7/1993 | Fushimi et al. |
| 5,250,542 A | 10/1993 | Cantrell et al. |
| 5,270,328 A | 12/1993 | Cantrell et al. |
| 5,298,410 A | 3/1994 | Phillips et al. |
| 5,320,840 A | 6/1994 | Camble et al. |
| 5,428,128 A | 6/1995 | Mensi-Fattohi et al. |
| 5,434,171 A | 7/1995 | Frank et al. |
| 5,442,043 A | 8/1995 | Fukuta et al. |
| 5,468,478 A | 11/1995 | Saifer et al. |
| 5,567,422 A | 10/1996 | Greenwald |
| 5,569,450 A | 10/1996 | Duan et al. |
| 5,612,460 A | 3/1997 | Zalipsky |
| 5,618,926 A | 4/1997 | Salamone et al. |
| 5,637,749 A | 6/1997 | Greenwald |
| 5,643,575 A | 7/1997 | Martinez et al. |
| 5,670,477 A | 9/1997 | Poduslo et al. |
| 5,714,639 A | 2/1998 | Bowman et al. |
| 5,854,208 A | 12/1998 | Jones et al. |
| 5,866,164 A | 2/1999 | Kuczynski et al. |
| 5,922,675 A | 7/1999 | Baker et al. |
| 5,972,954 A | 10/1999 | Foss et al. |
| 6,011,008 A | 1/2000 | Domb et al. |
| 6,316,644 B1 | 11/2001 | Chung et al. |
| 6,362,254 B2 | 3/2002 | Harris et al. |
| 6,380,405 B1 | 4/2002 | Ekwuribe et al. |
| 6,419,959 B1 | 7/2002 | Walter et al. |
| 6,451,806 B2 | 9/2002 | Farrar |
| 6,461,603 B2 | 10/2002 | Bentley et al. |
| 6,515,100 B2 | 2/2003 | Harris |
| 6,518,239 B1 | 2/2003 | Kuo et al. |
| 6,541,508 B2 | 4/2003 | Ekwuribe et al. |
| 6,565,885 B1 | 5/2003 | Tarara et al. |
| 6,703,381 B1 | 3/2004 | Ekwuribe et al. |
| 6,713,454 B1 | 3/2004 | Ekwuribe et al. |
| 6,713,488 B2 | 3/2004 | Sade et al. |
| 6,815,530 B2 | 11/2004 | Ekwuribe et al. |
| 6,835,802 B2 | 12/2004 | Ekwuribe et al. |
| 6,858,580 B2 | 2/2005 | Ekwuribe et al. |
| 6,903,082 B2 | 6/2005 | Ekwuribe et al. |
| 6,930,090 B2 | 8/2005 | Ekwuribe et al. |
| 6,943,148 B1 | 9/2005 | Ekwuribe et al. |
| 7,056,500 B2 | 6/2006 | Bentley et al. |
| 7,662,365 B2 | 2/2010 | Bentley et al. |
| 2002/0169125 A1 | 11/2002 | Leung et al. |
| 2002/0182172 A1 | 12/2002 | Bentley et al. |
| 2003/0044402 A1 | 3/2003 | Nelson |
| 2003/0105275 A1 | 6/2003 | Bentley et al. |
| 2003/0124086 A1 | 7/2003 | Bentley et al. |
| 2003/0161791 A1 | 8/2003 | Bentley et al. |
| 2003/0203961 A1 | 10/2003 | Ekwuribe et al. |
| 2004/0023852 A1 | 2/2004 | Roberts et al. |
| 2004/0082620 A1 | 4/2004 | Craig et al. |
| 2006/0105046 A1 | 5/2006 | Bentley et al. |
| 2009/0221766 A1 | 9/2009 | Cheng et al. |
| 2010/0105715 A1 | 4/2010 | Bentley et al. |

FOREIGN PATENT DOCUMENTS

| | | |
|---|---|---|
| EP | 0822218 | 2/1998 |
| EP | 0995757 | 4/2000 |
| JP | 01207320 | 8/1989 |
| WO | WO 93/24476 | 12/1993 |
| WO | WO 96/21469 | 7/1996 |
| WO | WO 97/14740 | 4/1997 |
| WO | WO 99/30727 A1 | 6/1999 |
| WO | WO 99/45964 | 9/1999 |
| WO | WO 01/12230 | 2/2001 |
| WO | WO 01/19407 | 3/2001 |
| WO | WO 01/47562 | 7/2001 |
| WO | WO 01/62299 | 8/2001 |
| WO | WO 02/43772 | 6/2002 |
| WO | WO 02/065988 | 8/2002 |
| WO | WO 02/089789 | 11/2002 |
| WO | WO 02/098949 | 12/2002 |
| WO | WO 03/032990 | 4/2003 |
| WO | WO 03/037384 | 5/2003 |
| WO | WO 03/037385 | 5/2003 |
| WO | WO 03/051113 | 6/2003 |
| WO | WO 03/079972 | 10/2003 |
| WO | WO 03/101476 | 12/2003 |
| WO | WO 2004/043396 | 5/2004 |
| WO | WO 2004/082620 | 9/2004 |
| WO | WO 2005/012335 A1 | 2/2005 |
| WO | WO 2005/016240 | 2/2005 |
| WO | WO 2005/051327 A2 | 6/2005 |
| WO | WO/2005/058367 | 6/2005 |

OTHER PUBLICATIONS

Batz et al., "Pharmakologisch aktive Polymere," Arzneimittel-Forshung 1977 pp. 1884-1888 (English summary provided).

Bennett et al., "Drug-Coupled Poly(Amino Acids) as Polymeric Prodrugs", Journal of Bioactive and Compatible Polymers, 1988, pp. 44-52, vol. 3.

Bennett et al., "Biodegradable Polymeric Prodrugs of Naltrexone", Journal of Controlled Release, 1991, pp. 43-52, vol. 16, Nos. 1/2.

Davies, et al., "Physiological Parameters in Laboratory Animals and Humans," Pharrn. Res. vol. 10, Issue 7, p. 1093-1095, 1993.

Donovan, et al., "Absorption of Polyethylene Glycols 600 Through 2000: The Molecular Weight Dependence of Gastrointestinal and Nasal Absorption," Pharrn. Res., vol. 7, Issue 8, 1990.

Eldon, et al., "NKTR-118 (Oral PEG-Naloxol), a PEGylated Derivative of Naloxone: Demonstrations of Selective Peripheral Opioid Antagonism After Oral Administration in Preclinical Models," Poster 28 presented at the American Academy of Pain Management 18th Annual Clinical Meeting; Sep. 27-30, 2007; Las Vegas, NV.

Enzon Pharmaceuticals, Macromolecular Engineering Technologies, pp. 1-14, (2004).

Erez et al, "Narcotic Antagonistic Potency of Bivalent Ligands Which Contain B-Naltrexarnine. Evidence for Bridging between Proximal Recognition Sites",J. Med. Chem., 1982, pp. 847-849, vol. 25, No. 7.

Ertl et al., "Fast Calculation of Molecular Polar Surface Area as a Sum of Fragment-Based Contributions and Its Application to the Prediction of Drug Transport Properties", J. Med. Chem., 2000; pp. 3714-3717, vol. 43.

Fishburn, et al., "The Pharmacology of PEGylation: Balancing PO with PK to Generate Novel Therapeutics," J. Pharm. Sci., p. 1-17,2008.

Fishman, J., et al., "Preparation and Evaluation of a Sustained Naloxone Delivery System in Rats", Pharmacology, 1975, pp. 513-519, vol. 13(6).

Flanagan et al., "Affinity Partitioning: A Method for Purification of Proteins Using Specific Polymer-Ligands in Aqueous Polymer Two-Phase Systems", The Journal of Biological Chemistry, 1975; pp. 1484-1489, vol. 250, No. 4.

Greenwald et al., "Drug Delivery Systems Employing 1,4- or 1,6-Elimination: Polyz(ethylene glycol) Prodrugs of Amine-Containing Compounds," J. Med. Chern., No. 42, p. 3657-3667 (1999).

Greenwald et al., "Drug Delivery Systems Based on Trimethyl Lock Lactonization: Poly(ethylene glycol) Prodrgus of Amino-Containing Compounds," J. Med Chern., No. 43, p. 475-487, (2000).

Greenwald, et al., "Effective drug delivery by PEGylated drug conjugates," Adv. Drug Deliv. Rev., vol. 55, p. 217-250, 2003.

Greenwald, R., et al., "Highly Water Soluble Taxol Derivatives: 7-Polyethylene Glycol Carbamates and Carbonates", J. Org. Chem., 1995, pp. 331-336, vol. 60.

Harris, et al., "Effect of PEGylation on Pharmaceuticals," Nat. Rev. Drug Discov., vol. 11, Issue. 3, p. 214-221, Mar. 2003.

Harris, et al., "Pegylation: A Novel Process for Modifying Pharmacokinetics," Clin. Pharmacokinet., vol. 40, No. 7, p. 539-551, 2001.

Harris, J. M., ed., "Poly(Ethylene Glycol) Chemistry—Biotechnical and Biomedical Applications," 1992, pp. 1-10, Plenum Press, New York.

Hayes et al., "Effect of β-funaltrexamine on opioid side-effects produced by morphine and U-50, 488H," J. Pharm. Pharmacol. (1985) 37, pp. 841-843.

He, et al., "Species Differences in Size Discrimination in the Paracellular Pathway Reflected by Oral Bioavailability ofPoly(ethylene glycol) and D-Peptides," J. Pharm. Sci., vol. 87, No. 5, p. 626-633, May 1998.

Jiang et al., "Stereochemical Studies on Medicinal Agents. 23. .sup.1 Synthesis and Biological Evaluation of 6-Amino Derivatives of Naloxone and Naltrexone", J. Medicinal Chemistry, 1977, pp. 1100-1103, vol. 20, No. 8.

Johansson et al., "Effect of some poly(ethylene glycol)-bound and dextran-bound affinity ligands on the partition of synaptic membranes in aqueous two-phase systems", J. Chromatogr. B, 1994, pp. 137-147, vol. 652.

Kelder et al., "Polar Molecular Surface as a Dominating Determinant for Oral Absorption and Brain Penetration of Drugs", Pharmaceutical Research, 1999; pp. 1514-1519, vol. 16, No. 10.

Lapicque et al., "Polysaccharidic Prodrugs for Enzymatically Controlled Release", Journal of Controlled Release, 1986, pp. 39-45, vol. 4.

Laverman, et al., "Preclinical and Clinical Evidence for Disappearance of Long-Circulating Characteristics of Polyethylene Glycol Liposomes at Low Lipid Dose," J. Pharmacol. Exp., vol. 293, No. 3, p. 996-1001, 2000.

Lee, et al., "Intranasal Delivery ofPEGylated Salmon Calcitonins: Hypocalcemic Effects in Rats," Calcif. Tissue Int., vol. 73, No. 6, p. 545-549, 2003.

Li et al., "Poly(.alpha.-Amino Acid)-Drug Conjugates-A Biodegradable Injectable Drug Delivery System", Polymer Preprints(American Chemical Society, Division of Polymer Chemistry), 1990, pp. 198-199, vol. 21, No. 2.

Mahkam et al., "Preparation of new biodegradable polyurethanes as a therapeutic agent", Polymer Degradation and Stability, 2003, pp. 199-202, vol. 80.

Murphy et al., "Opiod-induced Delay in Gastric Emptying: A Peripheral Mechanism in Humans," Anesthesiology (1997) 87, pp. 765-770.

Negishi et al., "Coupling of Naltrexone to Biodegradable Poly(.alpha.-Amino Acids)", Pharmaceutical Research, 1987, pp. 305-310, vol. 4, No. 4.

Nektar™—Transforming Therapuetics, Nektar Molecule Engineering: Polyethylene Glycol and Derivatives for Advanced PEGylation, pp. 1-20, (Catalog—2003).

Nektar™—Transforming Therapuetics, Nektar Molecule Engineering: Polyethylene Glycol and Derivatives for Advanced PEGylation, pp. 1-24, (Catalog—2004).

Nektar Therapeutics, "Nektar Announces Positive Results from Phase 2 Study of Oral NKTR-118 in Patients with Opioid-Induced Constipation (OIC)," PRNewswire dated Mar. 2, 2009.

Neumann et al., "Clinical Investigation of NKTR-118 as a Selective Oral Periphal Opioid Antagonist," Poster 27 Presented at the American Academy of Pain Management 18th Annual Clinical Meeting; Sep. 27-30, 2007; Las Vegas, NV.

NOF Corporation, "PEG Derivatives Phospholipid and Drug Delivery Materials for Pharmaceutics", pp. 1-46, (Catalogue 2003-1st).

NOF Corporation, "PEG Derivatives Phospholipid and Drug Delivery Materials for Pharmaceuticals", p. 1-46, (Catalogue 2003-2nd).

Olde et al., "Affinity Partitioning and Centrifugal Counter-Current Distribution of Membrane-Bound Opiate Receptors Using Naloxone-Poly(Ethylene Glycol)", Neuroscience, 1985, pp. 1247-1253, vol. 15, No. 4.

Pasternak et al., "Macromolecular Naloxone: A Novel Long-Acting Polymer-Bound Drug", Life Sciences, 1976, pp. 977-982, vol. 18.

Plasmatreat, Glossary, Last Accessed Sep. 11, 2009, http://www.plasmatreat.co.uk/glossary/glossary.html , 1 page.

Polypure, Products; PEG amines; PEG acids and amino acids; PEG thiols and disulfided; BIOTINS, (Apr. 2004).

Polypure, Products; PEG amines; PEG acids and amino acids; PEG thiols and disulfides; BIOTINS, (Apr. 2005).

Quanta Biodesign, Labeling, Derivatization and Crosslinking Reagents for Biological and Related Materials with dPEGTM, p. 1-38, (Mar. 12, 2004).

Quanta Biodesign, Labeling, Modification and Crosslinking Reagents incorporating our unique momodispersed dPEGTM Technology, p. 1-31, (Nov. 5, 2004).

Quanta Biosesign, Ltd., Leading innovator, producer and provider of monodisperse discrete PEGTM(dPEGTM) derivatives, (Product Catalog), p. 1-51, (Updated: Jul. 18, 2005).

Quanta Biosesign, Ltd., Leading innovator, producer and provider of monodisperse discrete PEG™ (dPEGTM) derivatives, (Product Catalog), p. 1-51, (Updated: Nov. 17, 2005).

Shearwater Polymers, Inc., p. 2-49, (Catalog—Mar. 1995).

Shearwater Polymers, Inc., Polyethylene Glycol and Derivatives, p. 1-53, (Catalog—Jul. 1997).

Shearwater Polymers, Inc., Polyethylene Glycol and Derivatives, p. 1-50, (Catalog—2000).

Shearwater Corporation, Polyethylene Glycol and Derivatives for Biomedical Applications, p. 1-17, (Catalog—2001).

Shin, et al., "Nasal Absorption and Pharmacokinetic Disposition of Salmon Calcitonin Modified with Low Molecular Weight Polyethylene Glycol," Chem. Pharm. Bull., vol. 52, No. 8, p. 957-960, 2004.

Sidman et al., "Use of Synthetic Polypeptides in the Preparation of Biodegradable Delivery Systems for Narcotic Antagonists", Synthetic Polypeptide Systems, 1980, pp. 214-231.

Takahasiii, R.N., et al., "Effects of Ketamine on Nociception and Gastrointestinal Motility in Mice Are Unaffected by Naloxone," pGen. Pharmac., 1987, pp. 201-203, vol. 18(2), Pergamon Journals Ltd.

Yamaoka, et al., "Distribution and Tissue Uptake of Poly(ethylene glycol) with Different Molecular Weights after Intravenous Administration to Mice," J. Pharm. Sci., vol. 83, No. 4, p. 601-606, Apr. 1994.

Yamashita et al., "Micelle Monomer Control over the Membrane-Disrupting Properties of an Amphiphilic Antibiotic", J. Am. Chem. Soc., 1995; pp. 6249-6253, vol. 117.

Yolles, S., et al., "Long Acting Delivery Systems for Narcotic Antagonists II: Release Rates of Naltrexone from Poly(lactic Acid) Composites," Journal of Pharmaceutical Sciences, Feb. 1975, pp. 348-349, vol. 64(2).

Yuan, et al., "Methylnaltrexone prevents morphine-induced delay in oral-cecal transit time without affecting analgesia: a double—blind randomized placebo-controlled trial," Clin Pharmacol Ther (1996) 59, pp. 469-475.

Zalipsky, S., "Functionalized Poly(ethylene glycol) for Preparation of Biologically Relevant Conjugates," Bioconjugate Chem., 1995, pp. 150-165, vol. 6, American Chemical Society, USA.

Zalipsky, Samuel., "Chemistry of Polyethylene Glycol Conjugates with Biologically Active Molecules", Advanced Drug Delivery Reviews, 1995, pp. 157-182, vol. 16.

Australian Government IP Australia, Examiner's First Report on patent application No. 2004299138 dated Feb. 18, 2009.

Mexican Office Action (Jun. 24, 2009) for application No. PA/a/2006/006914 with informal English Translation.

ISA, International Search Report and Written Opinion dated Nov. 28, 2005 for PCT/US04/042661.

USPTO, Office action dated Apr. 7, 2009 for U.S. Appl. No. 11/332,964.

USPTO, Office action dated Nov. 9, 2007 for U.S. Appl. No. 11/332,964.

USPTO, Office action dated Jul. 3, 2006 for U.S. Appl. No. 11/332,964.

USPTO, Final Office action dated Oct. 12, 2006 for U.S. Appl. No. 11/332,964.

Applicant response dated Nov. 20, 2009 to USPTO non-final rejection dated Apr. 7, 2009 for U.S. Appl. No. 11/332,964.

EPO, Communication pursuant to Article 94(3) EPC dated Nov. 2, 2010 for Application No. 04 814 802.7.

Note: Blood Brain Barrier perfusion rate in pmole/gm/sec

CHEMICALLY MODIFIED SMALL MOLECULES

CROSS REFERENCE TO RELATED APPLICATION

This application is a continuation of U.S. patent application Ser. No. 11/015,196, filed Dec. 16, 2004, now U.S. Pat. No. 7,786,133, which claims the benefit of priority to U.S. Provisional Patent Application Ser. No. 60/530,122, filed Dec. 16, 2003, both of which are-incorporated herein by reference.

FIELD OF THE INVENTION

This invention provides chemically modified small molecules and related methods that possess certain advantages over small molecules lacking the chemical modification. The chemically modified small molecules described herein relate to and/or have application(s) in the fields of drug discovery, pharmacotherapy, physiology, organic chemistry, polymer chemistry, and others.

BACKGROUND OF THE INVENTION

The use of proteins as active agents has expanded in recent years due to several factors: improved techniques for identifying, isolating, purifying and/or recombinantly producing proteins; increased understanding of the roles of proteins in vivo due to the emergence of proteonomics; and improved formulations, delivery vehicles and approaches for chemically modifying proteins to enhance their pharmacokinetic or phamacodynamic properties. With respect to improved approaches for chemically modifying proteins, covalent attachment of a polymer such as poly(ethylene glycol) or PEG to a protein has been used to improve the circulating half-life, decrease immunogenicity, and/or reduce proteolytic degradation. This approach of covalently attaching PEG to a protein or other active agent is commonly referred to as PEGylation. Proteins for injection that are modified by covalent attachment of PEGs are typically modified by attachment of relatively high molecular weight PEG polymers that often range from about 5,000 to about 40,000 Daltons.

While modification of relatively large proteins for the purpose of improving their pharmaceutical utility is perhaps one of the most common applications of PEGylation, PEGylation has also been used, albeit to a limited degree, to improve the bioavailability and ease of formulation of small molecule drugs having poor aqueous solubilities. For instance, water-soluble polymers such as PEG have been covalently attached to artilinic acid to improve its aqueous solubility. See, for example, U.S. Pat. No. 6,461,603. Similarly, PEG has been covalently attached to triazine-based compounds such as trimelamol to improve their solubility in water and enhance their chemical stability. See, for example, International Patent Publication WO 02/043772. Covalent attachment of PEG to bisindolyl maleimides has been employed to improve poor bioavailability of such compounds due to low aqueous solubility. See, for example, International Patent Publication WO 03/037384. PEG chains attached to small molecule drugs for the purpose of increasing their aqueous solubility are typically of sizes ranging from about 500 Daltons to about 5000 Daltons, depending upon the molecular weight of the small molecule drug.

Active agents can be dosed by any of a number of administration routes including injection, oral, inhalation, nasal, and transdermal. One of the most preferred routes of administration, due to its ease, is oral administration. Oral administration, most common for small molecule drugs (i.e., non-protein-based drugs), is convenient and often results in greater patient compliance when compared to other routes of administration. Unfortunately, many small molecule drugs possess properties (e.g., low oral bioavailability) that render oral administration impractical. Often, the properties of small molecule drugs that are required for dissolution and selective diffusion through various biological membranes directly conflict with the properties required for optimal target affinity and administration. The primary biological membranes that restrict entrance of small molecule drugs into certain organs or tissues are membranes associated with certain physiological barriers, e.g., the blood-brain barrier, the blood-placental barrier, and the blood-testes barrier.

The blood-brain barrier protects the brain from most toxicants. Specialized cells called astrocytes possess many small branches, which form a barrier between the capillary endothelium and the neurons of the brain. Lipids in the astrocyte cell walls and very tight junctions between adjacent endothelial cells limit the passage of water-soluble molecules. Although the blood-brain barrier does allow for the passage of essential nutrients, the barrier is effective at eliminating the passage of some foreign substances and can decrease the rate at which other substances cross into brain tissue.

The placental barrier protects the developing and sensitive fetus from many toxicants that may be present in the maternal circulation. This barrier consists of several cell layers between the maternal and fetal circulatory vessels in the placenta. Lipids in the cell membranes limit the diffusion of water-soluble toxicants. Other substances such as nutrients, gases, and wastes of the developing fetus can, however, pass through the placental barrier. As in the case of the blood-brain barrier, the placental barrier is not totally impenetrable but effectively slows down the diffusion of many toxicants from the mother to the fetus in the art.

For many orally administered drugs, permeation across certain biological membranes such as the blood-brain barrier or the blood-placental barrier is highly undesirable and can result in serious side-effects such as neurotoxicity, insomnia, headache, confusion, nightmares or teratogenicity. These side effects, when severe, can be sufficient to halt the development of drugs exhibiting such undesirable brain or placental uptake. Thus, there is a need for new methods for effectively delivering drugs, and in particular small molecule drugs, to a patient while simultaneously reducing the adverse and often toxic side-effects of small molecule drugs. Specifically, there is a need for improved methods for delivering drugs that possess an optimal balance of good oral bioavailability, bioactivity, and pharmacokinetic profile. The present invention meets this and other needs.

SUMMARY OF THE INVENTION

The present invention is based upon the development and discovery of chemically modified small molecule drugs having unique properties (such as lower rates of crossing a biological membrane), as well as methods for preparing and administering such compounds.

In one aspect, the invention provides a composition comprised of monodisperse or bimodal conjugates, each conjugate comprised of a moiety derived from a small molecule drug covalently attached by a stable linkage to a water-soluble oligomer. Preferably, the oligomer is obtained from a monodisperse (i.e., unimolecular) or bimodal, or even trimodal or tetramodal composition. Conjugates prepared from a monodisperse oligomer composition are referred to as monodisperse conjugates, conjugates prepared from a bimodal oligomer composition are referred to as bimodal conjugates, and so forth.

Advantageously, the water-soluble oligomer, when attached to the small molecule drug, effectively diminishes the ability of the resulting conjugate to cross certain biological membranes, such as those associated with the blood-brain barrier or the blood-placental barrier. In one or more embodiments, a conjugate is provided that exhibits a reduced biological membrane crossing rate as compared to the biological membrane crossing rate of the small molecule drug not attached to the water-soluble oligomer.

The conjugate can be described generally as having a structure O-X-D, wherein O corresponds to the water-soluble oligomer, X corresponds to a stable linkage, and D corresponds to a moiety derived from the small molecule drug.

In one or more embodiments, the small molecule drug is orally bioavailable. In addition, the conjugate is also orally bioavailable. In those situations where both the small molecule drug and the corresponding small molecule drug-oligomer conjugate are bioavailable, it is preferred that the conjugate possesses an oral bioavailability that is at least 10% of the oral bioavailability of the small molecule drug in unconjugated form. Exemplary percentages of oral bioavailability retained by the conjugate as compared to the small molecule drug in unconjugated form include the following: at least about 20%; at least about 30%; at least about 40%; at least about 50%; at least about 60%; at least about 70%; at least about 80%; and at least about 90%.

In one or more embodiments, administration of the conjugate exhibits a reduction in first pass metabolism as compared to the corresponding small molecule drug in unconjugated form. Thus, the invention provides (among other things) for a method for reducing the metabolism of an active agent, the method comprising the steps of: providing monodisperse or bimodal conjugates, each conjugate comprised of a moiety derived from a small molecule drug covalently attached by a stable linkage to a water-soluble oligomer, wherein said conjugate exhibits a reduced rate of metabolism as compared to the rate of metabolism of the small molecule drug not attached to the water-soluble oligomer; and administering said conjugate to a patient.

Water-soluble oligomers for use in preparing conjugates can vary and the invention is not particularly limited in this regard, Exemplary oligomers include oligomers composed of monomers selected from the group consisting of alkylene oxide, olefinic alcohol, vinylpyrrolidone, hydroxyalkylmethacrylamide, hydmxyalkylmethacrylate, saccharide, α-hydroxy acid, phosphazene, oxazoline, amino acids, monosaccharides, and N-acryloylmorpholine. In one or more preferred embodiments, the water-soluble oligomer is composed of ethylene oxide monomers.

The oligomer portion of the conjugates provided herein is composed of individual monomers attached in series. Exemplary oligomers can contain a number of repeating monomers in series, the number of monomers satisfying one or more of the following ranges: 1-25; 1-20; 1-15; 1-12; 1-10; and 2-9. The oligomer can possess a number of monomers corresponding to any one of the following values: 1; 2; 3; 4; 5; 6; 7; 8; 9; 10; 11; and 12.

The oligomer portion of the conjugates provided herein can have various geometries, structures and features. Non-limiting examples include straight and branched oligomer architectures.

In one or more embodiments, the conjugates provide herein each have a single water-soluble oligomer covalently attached to a single moiety derived from the small molecule drug. That is, the ratio of oligomer to moiety derived from the small molecule drug is 1:1. In one or more additional embodiments, however, the conjugate may possess 1, 2, or 3 oligomers covalently attached to the moiety derived from the small molecule drug.

The linkage connecting the water-soluble oligomer and the moiety derived from a small molecule drug can be any suitable linkage to bind molecules, although a covalent linkage (through one or more atoms) is preferred. Suitable covalent linkages between the water-soluble oligomer and the small molecule drug include, without limitation, the following: ether; amide; urethane; amine; thioether; and a carbon-carbon bond.

The compositions provided herein can comprise only a single species of conjugate or the compositions can comprise two, three, four or more species of different conjugates. For example, the composition can comprise a single species of conjugate such that other conjugate species (e.g., conjugate species having differences in molecular weight, molecular structure and so forth) are substantially absent. In addition, the compositions provided herein can also contain, for example, two different species of conjugates mixed together wherein (a) the same moiety derived from a small molecule drug is present in all of the conjugates in the composition, and (b) the oligomer size of one species of conjugate is different from the oligomer size of the other species of conjugate. For those compositions comprising mixtures having different conjugate species, each species will be present in the composition in a known and defined amount. Although the species of conjugates in any given composition can differ in the oligomer size as described above, differences in conjugate species can also be based on the oligomer type, moiety derived from the small molecule drug, stereoisomer of the conjugate, and so forth.

In another aspect of the invention, there is provided a method for administering a composition described herein. In this respect, the method comprises the step of administering a composition comprised of monodisperse or bimodal conjugates, each conjugate comprised of a moiety derived from a small molecule drug covalently attached by a stable linkage to a water-soluble oligomer, wherein the conjugate exhibits a reduced biological membrane crossing rate as compared to the biological membrane crossing rate of the small molecule drug not attached to the water-soluble oligomer. Conveniently, the administering step is selected from any of a number of administration approaches including, for example, those selected from the group consisting of oral administration, transdermal administration, buccal administration, transmucosal administration, vaginal administration, rectal administration, parenteral administration, and pulmonary administration In yet another aspect, a method is provided for optimizing the selective biological membrane crossing of a small molecule drug. In this regard, the method comprises the step of conjugating a water-soluble oligomer from a monodisperse or bimodal oligomer composition to a small molecule drug via a stable covalent linkage, to thereby form a conjugate that exhibits a biological membrane crossing rate that is reduced when compared to the biological membrane crossing rate of the small molecule drug prior to said conjugating.

In still another aspect of the invention, there is provided a method for optimizing a reduction in biological membrane crossing of a small molecule drug, said method comprising the steps of: (a) preparing a series of monodisperse or bimodal conjugates, each conjugate in the series comprised of a moiety derived from a small molecule drug covalently attached by a stable linkage to a water-soluble oligomer, wherein each conjugate in the series differs only in size of the oligomer as based on the number of monomers in the oligomer; (b) characterizing, for each conjugate in the series prepared in step (a), the extent to which the conjugate does not cross the biological membrane; and (c) based upon the results from (b), identifying the conjugate from the series of conjugates prepared in step (a) that possesses the optimal reduction in biological membrane crossing.

The invention also provides a method for preparing a conjugate, the method comprising the step of covalently attaching a water-soluble oligomer obtained from a monodisperse or bimodal oligomer composition to a small molecule drug. In this way, a conjugate is created comprised of a stable linkage connecting the oligomer to a moiety derived from the small molecule drug. An exemplary approach for providing a conjugate comprises the steps of reacting, in one or more synthetic steps, a water-soluble oligomer from a monodisperse or polymodal oligomer composition, wherein the oligomer has a reactive group, A, with a small molecule drug comprising a reactive group, B, suitable for reaction with A, under conditions effective to form a hydrolytically stable linkage resulting from the reaction of A with B, to thereby form a small molecule drug-water soluble oligomer conjugate.

To the extent that the method for preparing a conjugate results in a mixture of isomers (or other conjugate species), the additional step of separating the isomers (or other conjugate species) to obtain a single conjugate isomer (or conjugate species) can be carried out. Optionally, for any two or more compositions wherein each composition has a single conjugate isomer (or conjugate species), the step of combining the two or more separate compositions can be performed to provide a composition having known and defined amounts of each conjugate isomer (or conjugate species).

The invention also provides a method for preparing a monodisperse water-soluble oligomer, such as oligo(ethylene oxide). The method includes the steps of reacting a halo-terminated oligo(ethylene oxide) having (m) monomers with a hydroxyl-terminated oligo(ethylene oxide) having (n) monomers under conditions effective to displace the halo group to form a monomeric oligo(ethylene oxide) having (m)+(n) monomer subunits ($OEG_{m+n}$), where (m) and (n) each independently range from 1 to 10. Preferably, although not necessarily, (m) ranges from 2-6 (more preferably 1-3) and (n) ranges from 2-6.

The method for preparing monodisperse water-soluble oligomers is generally carried out in the presence of a strong base such as sodium, potassium, sodium hydride, potassium hydride, sodium methoxide, potassium methoxide, sodium tert-butoxide, or potassium tert-butoxide, suitable for converting the hydroxyl group of the hydroxyl-terminated oligo (ethylene glycol) into the corresponding alkoxide.

With respect to the halo (or halogen group) associated with a halo-terminated oligo(ethylene oxide) (or other halo-terminated oligomer), the halo is typically selected from the group consisting of chloro, bromo and iodo. In addition, the halo-terminated oligo(ethylene oxide) is typically end capped with, for example, a methyl or ethyl group to provide the corresponding methyl or ethyl ether terminus. A preferred halo-terminated oligo(ethylene oxide) is $H_3CO—(CH_2CH_2O)_m—Br$, where (m) is defined as above.

With respect to a hydroxyl-terminated oligo(ethylene oxide), such hydroxyl-terminated oligo(ethylene oxide)s correspond to the structure $HO—(CH_2CH_2O)_n—H$, where (n) is as described above.

The method for preparing monodisperse water-soluble oligomers can also comprise the step of converting the terminal hydroxyl group of $OEG_{m+n}$ into a halo group to form $OEG_{m+n}$-X, where X is a halo group. This can be followed by reaction of $OEG_{m+n}$-X with a hydroxyl-terminated oligo(ethylene oxide) having (n) monomers under conditions effective to displace the halo group to thereby form an oligo (ethylene oxide) having (m)+2(n) monomer subunits ($OEG_{m+2n}$), where (m) and (n) are as previously described. Optionally, the above steps can be repeated until a monodisperse oligo(ethylene oxide) having a desired, discrete number of monomer is obtained.

Also provided is a method for preparing a conjugate using a monodisperse oligo(ethylene oxide) composition prepared as described above. While preferred for use in preparing conjugates of the present invention, monodisperse oligomers of ethylene oxide as described above can be used for attachment to any of a number of active agents or surfaces. Preferred bioactive agents for coupling with a monodisperse oligo(ethylene oxide) prepared by the above method include small molecule therapeutics, diagnostic agents, dyes, imaging agents, targeting agents, surfactants, cosmetics, cosmeceuticals, neutriceuticals, and the like.

These and other objects, aspects, embodiments and features of the invention will become more fully apparent when read in conjunction with the following detailed description.

DETAILED DESCRIPTION OF THE INVENTION

Figure 1:
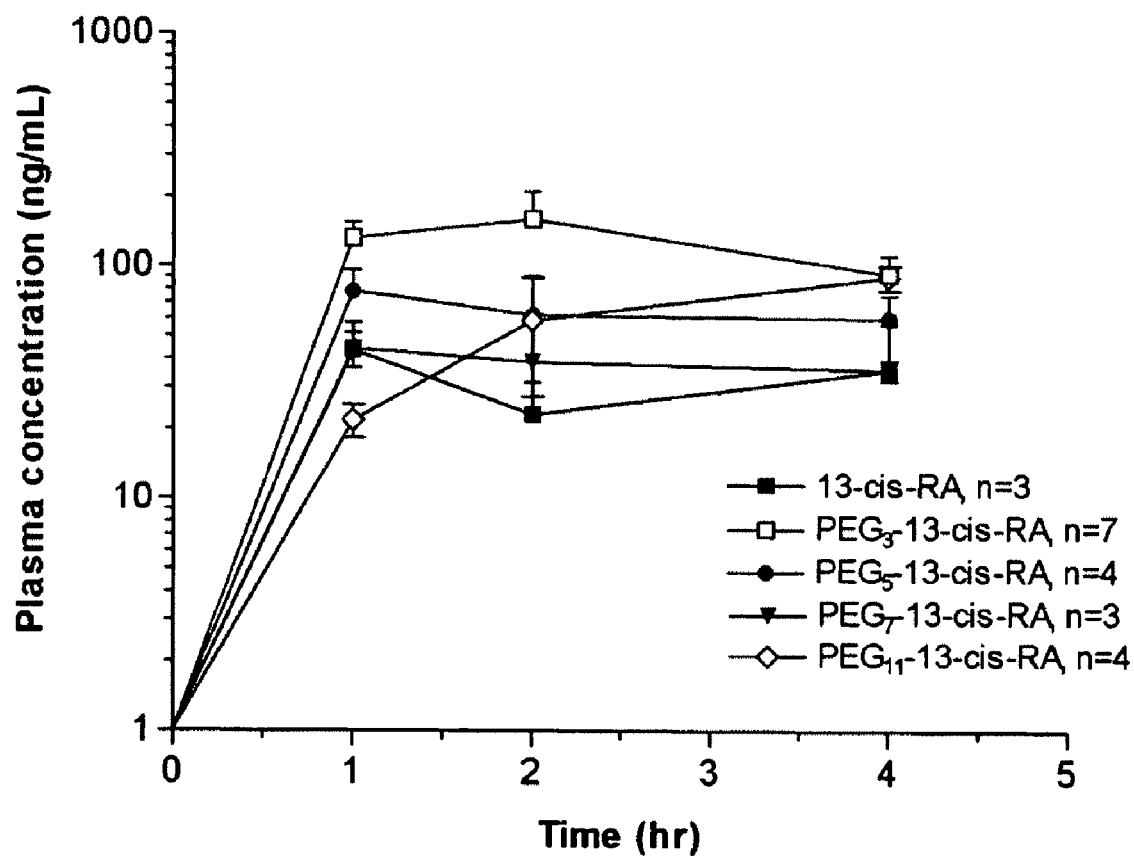
FIG. 1 is a plot of plasma concentration versus time for 13-cis retinoic acid ("13-cis-RA") and exemplary small PEG conjugates thereof ($PEG_3$-13-cis retinamide, "$PEG_3$-13-cis RA"; $PEG_5$-13-cis retinamide, "$PEG_5$-13-cis RA; $PEG_7$-13-cis retinamide, "$PEG_7$-13-cis RA; and $PEG_{11}$-13-cis retinamide, "$PEG_{11}$-13-cis RA") administered to Sprague Dawley rats as described in detail in Example 7.

It must be noted that, as used in this specification, the singular forms "a," "an," and "the" include plural referents unless the context clearly dictates otherwise.

In describing and claiming the present invention, the following terminology will be used in accordance with the definitions described below.

"Water soluble" as in a "water-soluble oligomer" indicates an oligomer that is at least 35% (by weight) soluble, and preferably greater than 95% soluble, in water at room temperature. Typically, an unfiltered aqueous preparation of a "water-soluble" oligomer transmits at least 75%, more preferably at least 95%, of the amount of light transmitted by the same solution after filtering. On a weight basis, a "water soluble" oligomer is preferably at least 35% (by weight) soluble in water, more preferably at least 50% (by weight) soluble in water, still more preferably at least 70% (by weight) soluble in water, and still more preferably at least 85% (by weight) soluble in water. It is most preferred, however, that the water-soluble oligomer is at least 95% (by weight) soluble in water or completely soluble in water.

The terms "monomer," "monomeric subunit" and "monomeric unit" are used interchangeably herein and refer to one of the basic structural units of a polymer or oligomer. In the case of a homo-oligomer, this is defined as a structural repeating unit of the oligomer. In the case of a co-oligomer, a monomeric unit is more usefully defined as the residue of a monomer which was oligomerized to form the oligomer, since the structural repeating unit can include more than one type of monomeric unit. Preferred oligomers of the invention are homo-oligomers.

An "oligomer" is a molecule possessing from about 1 to about 30 monomers. The architecture of an oligomer can vary. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" or an oligoethylene glycol is one in which all of the monomer subunits are ethylene oxide subunits. Typically, substantially all, or all, monomeric subunits are ethylene oxide subunits, though the oligomer may contain distinct end capping moieties or functional groups, e.g. for conjugation. Typically, PEG oligomers for use in the present invention will comprise one of the two following structures: "—(CH$_2$CH$_2$O)$_n$—" or "—(CH$_2$CH$_2$O)$_{n-1}$CH$_2$CH$_2$—," depending upon whether or not the terminal oxygen(s) has been displaced, e.g., during a synthetic transformation. As stated above, for the PEG oligomers of the invention, the variable (n) ranges from 1 to 30, and the terminal groups and architecture of the overall PEG can vary. When PEG further comprises a functional group, A, for linking to, e.g., a small molecule drug, the functional group when covalently attached to a PEG oligomer, does not result in formation of (i) an oxygen-oxygen bond (—O—O—, a peroxide linkage), or (ii) a nitrogen-oxygen bond (N—O, O—N).

An "end capping group" is generally a non-reactive carbon-containing group attached to a terminal oxygen of a PEG oligomer. For the purposes of the present invention, preferred are capping groups having relatively low molecular weights such as methyl or ethyl. The end-capping group can also comprise a detectable label. Such labels include, without limitation, fluorescers, chemiluminescers, moieties used in enzyme labeling, colorimetric labels (e.g., dyes), metal ions, and radioactive moieties.

"Branched", in reference to the geometry or overall structure of an oligomer, refers to an oligomer having two or more polymer "arms" extending from a branch point.

"Forked" in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions effective to produce a desired reaction in the reaction mixture.

A "protecting group" is a moiety that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof is meant to encompass protected forms thereof.

A "physiologically cleavable" or "hydrolyzable" or "degradable" bond is a relatively labile bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, thiolesters, and carbonates.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Monodisperse" refers to an oligomer composition wherein substantially all of the oligomers in the composition have a well-defined, single (i.e., the same) molecular weight and defined number of monomers, as determined by chromatography or mass spectrometry. Monodisperse oligomer compositions are in one sense pure, that is, substantially having a single and definable number (as a whole number) of monomers rather than a large distribution. A monodisperse oligomer composition of the invention possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a large distribution and would possess a MW/Mn value of 1.0005, and more preferably, a MW/Mn value of 1.0000 if the oligomer were not attached to the moiety derived from a small molecule drug. A composition comprised of monodisperse conjugates can, however, include one or more nonconjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a large distribution, and whose distribution of molecular weights, when plotted as a number fraction versus molecular weight, appears as two separate identifiable peaks. Preferably, for a bimodal oligomer composition as described herein, each peak is symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and most preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1,0005 or less, and most preferably a MW/Mn value of 1.0000 if the oligomer were not attached to the moiety derived from a small molecule drug. A composition comprised of bimodal conjugates can, however, include one or more nonconjugate substances such as solvents, reagents, excipients, and so forth A "small molecule drug" is broadly used herein to refer to an organic, inorganic, or organometallic compound typically having a molecular weight of less than about 1000. Small molecule drugs of the invention encompass oligopeptides and other biomolecules having a molecular weight of less than about 1000.

The terms "moiety derived from a small molecule drug" and "small molecule drug moiety" are used interchangeably herein to refer to the portion or residue of the parent small molecule drug up to the covalent linkage resulting from covalent attachment of the drug (or an activated or chemically modified form thereof) to an oligomer of the invention.

A "biological membrane" is any membrane, typically made from specialized cells or tissues, that serves as a barrier to at least some xenobiotics or otherwise undesirable materials. As used herein a "biological membrane" includes those membranes that are associated with physiological protective barriers including, for example: the blood-brain barrier; the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, rectal mucosa, and so forth). Unless the context clearly dictates otherwise, the term "biological membrane" does not include those membranes associated with the middle gastro-intestinal tract (e.g., stomach and small intestines).

A "biological membrane crossing rate," as used herein, provides a measure of a compound's ability to cross a biological barrier, such as the blood-brain barrier ("BBB"). A variety of methods can be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known, described herein and/or in the relevant literature, and/or can be determined by one of ordinary skill in the art.

A compound that "crosses the blood-brain barrier" in accordance with the invention is one that crosses the BBB at a rate greater than that of atenolol using the methods as described herein.

A "reduced rate of metabolism" in reference to the present invention, refers to a measurable reduction in the rate of metabolism of a water-soluble oligomer-small molecule drug conjugate as compared to rate of metabolism of the small molecule drug not attached to the water-soluble oligomer (i.e., the small molecule drug itself) or a reference standard material. In the special case of "reduced first pass rate of metabolism," the same "reduced rate of metabolism" is required except that the small molecule drug (or reference standard material) and the corresponding conjugate are administered orally. Orally administered drugs are absorbed from the gastro-intestinal tract into the portal circulation and must pass through the liver prior to reaching the systemic circulation. Because the liver is the primary site of drug metabolism or biotransformation, a substantial amount of drug can be metabolized before it ever reaches the systemic circulation. The degree of first pass metabolism, and thus, any reduction thereof, can be measured by a number of different approaches. For instance, animal blood samples can be collected at timed intervals and the plasma or serum analyzed by liquid chromatography/mass spectrometry for metabolite levels. Other techniques for measuring a "reduced rate of metabolism" associated with the first pass metabolism and other metabolic processes are known, described herein and/or in the relevant literature, and/or can be determined by one of ordinary skill in the art. Preferably, a conjugate of the invention can provide a reduced rate of metabolism reduction satisfying at least one of the following values: at least about 5%, at least about 10%, at least about 15%; least about 20%; at least about 25%; at least about 30%; at least about 40%; at least about 50%; at least about 60%; at least about 70%; at least about 80%; and at least about 90%.

A compound (such as a small molecule drug or conjugate thereof) that is "orally bioavailable" is one that possesses a bioavailability when administered orally of greater than 1%, and preferably greater than 10%, where a compound's bioavailability is the fraction of administered drug that reaches the systemic circulation in unmetabolized form.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, i-butyl, t-butyl "Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, benzyl, etc.), preferably $C_1$-$C_7$.

"Electrophile" refers to an ion, atom, or an ionic or neutral collection of atoms having an electrophilic center, i.e., a center that is electron seeking, capable of reacting with a nucleophile.

"Nucleophile" refers to an ion or atom or an ionic or neutral collection of atoms having a nucleophilic center, i.e., a center that is seeking an electrophilic center, and capable of reacting with an electrophile.

"Drug" as used herein includes any agent, compound, composition of matter or mixture which provides some pharmacologic, often beneficial, effect that can be demonstrated in vivo or in vitro. This includes foods, food supplements, nutrients, nutriceuticals, drugs, vaccines, antibodies, vitamins, and other beneficial agents. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a water-soluble oligomer-small molecule drug conjugate present in a composition that is needed to provide a desired level of active agent and/or conjugate in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterobifunctional.

A basic or acidic reactant described herein includes neutral, charged, and any corresponding salt forms thereof.

The term "patient," refers to a living organism suffering from or prone to a condition that can be prevented or treated by administration of a conjugate as described herein, typically, but not necessarily, in the form of a water-soluble oligomer-small molecule drug conjugate, and includes both humans and animals.

"Optional" or "optionally" means that the subsequently described circumstance may or may not occur, so that the description includes instances where the circumstance occurs and instances where it does not.

The present invention is directed to (among other things) compositions of small molecule drugs that are chemically modified by covalent attachment of a water-soluble oligomer obtained from a monodisperse or bimodal composition of water-soluble oligomers. Because the water-soluble oligomer is obtained from a monodisperse or bimodal composition of water-soluble oligomers, the resulting small molecule drug-oligomer compositions of the invention are exceedingly pure and well-defined from a structural standpoint.

An advantage of the conjugates described herein is their ability to exhibit a reduced biological membrane crossing rate as compared to the corresponding active agent not in conjugated form. While not wishing to be bound by theory, it is believed that molecular size is an important factor for determining whether and to what extent any given molecule can pass or cross any given biological membrane. For example, most if not all protective barriers, rely at least in part on highly packed cells that form a membrane having tight junctions through which only relatively small molecules can pass. Thus, for a given small molecule drug, the attachment of a water-soluble polymer to the small molecule drug provides a conjugate that is necessarily larger and with the expectation that the conjugate will either be prevented from crossing a biological membrane or will have a reduced biological membrane crossing rate as compared to the unconjugated small molecule drug.

As will be shown in further detail below and in the Experimental section, however, reducing the rate of biological membrane crossing by increasing molecular size by conjugating a water-soluble oligomer to a small molecule drug does not typically provide a completely satisfactory conjugate. Ideally, the conjugate will be provided as a composition comprising monodisperse or bimodal conjugates. Again, while not wishing to be bound by theory, it is believed that even very small differences in the number of monomers between conjugates can provide relatively large differences in properties such as pharmacologic activity, metabolism, oral bioavailability, biological membrane crossing rate, solubility and others.

Figure 10:
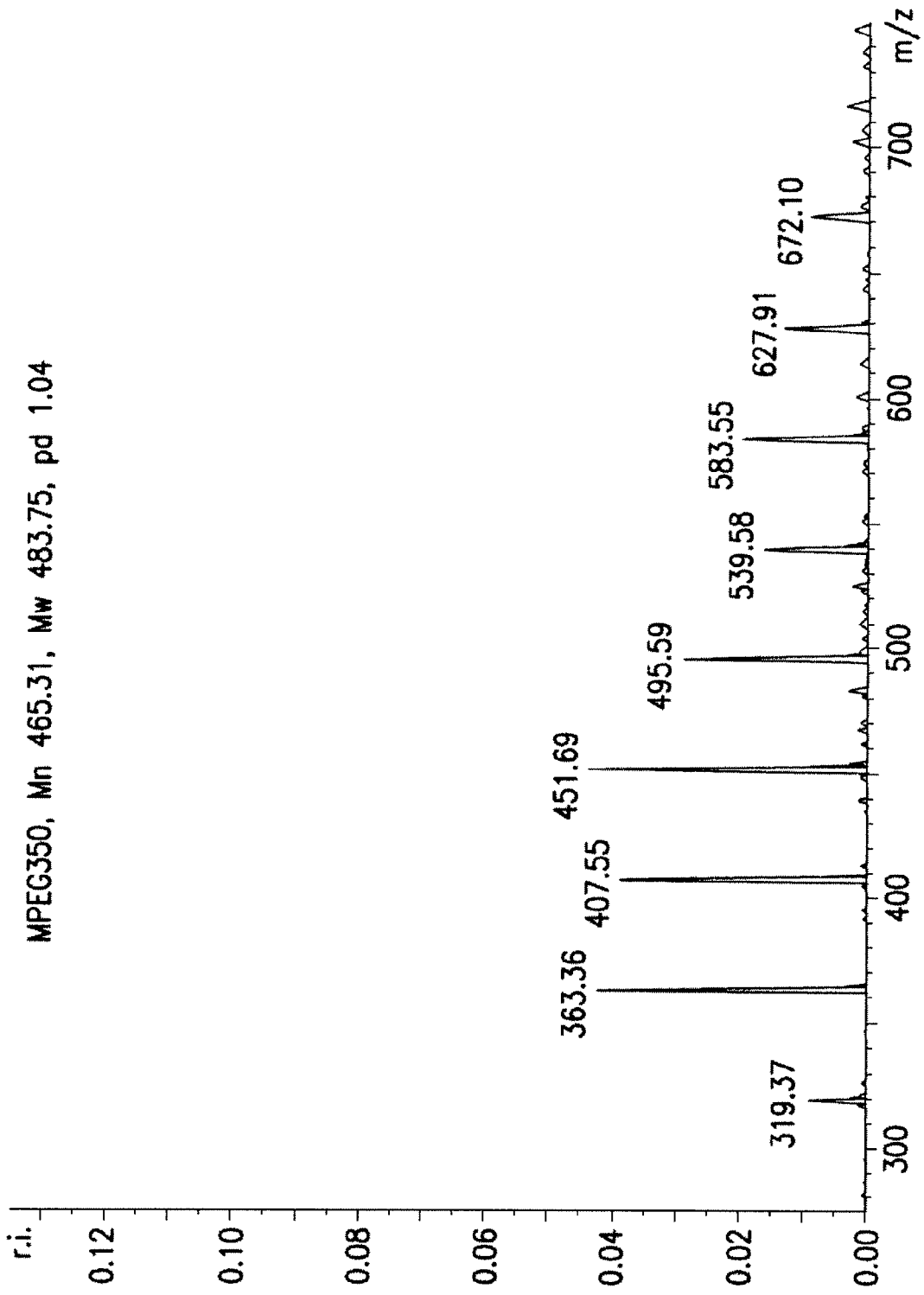
FIG. 10 is mass spectrum of methoxy-PEG-350 obtained from a commercial source (Sigma-Aldrich). As can be seen from the analysis, although the reagent is sold as methoxy-PEG having a molecular weight of 350, the reagent is actually a mixture of 9 distinct PEG oligomers, with the number of monomer subunits ranging from approximately 7 to approximately 15.

Furthermore, as is evidenced by the mass spectrum provided in FIG. 10, commercially available oligomer compositions such as PEG-350 are, in fact, relatively impure in that a range of oligomer sizes are present in the composition. Thus, the use of such relatively impure oligomer compositions (without further purification) in the synthesis of conjugates would result in a wide range of conjugate molecular weights sizes (as a result of the wide range of molecular weights in the composition used to form the conjugate). As a consequence, the resulting conjugate composition comprises many species of conjugates, wherein each conjugate would be expected to have different properties. From a regulatory and medicinal perspective, compositions comprising moieties having markedly different properties are ideally avoided.

As a result, the present invention provides conjugates that are not only relatively large (as compared to the corresponding unconjugated small molecule drug) to reduce biological membrane crossing (again, as compared to the corresponding unconjugated small molecule drug), but are substantially pure as well to ensure consistent and desired activity and other properties of the composition. Thus, a composition is provided comprising monodisperse or bimodal conjugates, each conjugate comprised of a moiety derived from a small molecule drug covalently attached by a stable linkage to a water-soluble oligomer, wherein said conjugate exhibits a reduced biological membrane crossing rate as compared to the biological membrane crossing rate of the small molecule drug not attached to the water-soluble oligomer.

As previously indicated, use of discrete oligomers from a well-defined composition of oligomers to form conjugates can advantageously alter certain properties associated with the corresponding small molecule drug. For instance, a conjugate of the invention, when administered by any of a number of suitable administration routes, such as parenteral, oral, transdermal, buccal, pulmonary, or nasal, exhibits reduced penetration across a biological membrane (such as the biological membranes associated with the blood-brain barrier and blood-placental barrier). It is preferred that the conjugates exhibit slowed, minimal or effectively no crossing of biological membranes (such as the biological membranes associated with the blood-brain barrier and blood-placental barrier), while still crossing the gastro-intestinal (GI) walls and into the systemic circulation if oral delivery is intended. If pulmonary delivery is intended, the conjugate administered will preferably have no crossing into systemic circulation or a reduced pulmonary tissue-blood barrier crossing rate so that local lung levels are maintained for local pharmacologic activity in the lung. Moreover, the conjugates of the invention maintain a degree of bioactivity as well as bioavailability in their conjugated form.

With respect to the blood-brain barrier ("BBB"), this barrier restricts the transport of drugs from the blood to the brain. This barrier consists of a continuous layer of unique endothelial cells joined by tight junctions. The cerebral capillaries, which comprise more than 95% of the total surface area of the BBB, represent the principal route for the entry of most solutes and drugs into the central nervous system.

Although it may be desirable for some compounds to achieve adequate concentrations in brain tissue to pharmacologically act therein, many other compounds that have no useful pharmacologic activity in brain tissue can ultimately reach the tissues of the central nervous system. By reducing the crossing rate of entry of these non-centrally acting compounds into the central nervous system, the risk of central nervous system side effects is reduced and the therapeutic effect may even be increased.

For compounds whose degree of blood-brain barrier crossing ability is not readily known, such ability can be determined using a suitable animal model such as an in situ rat brain perfusion ("RBP") model as described herein. Briefly, the RBP technique involves cannulation of the carotid artery followed by perfusion with a compound solution under controlled conditions, followed by a wash out phase to remove compound remaining in the vascular space. (Such analyses can be conducted, for example, by contract research organizations such as Absorption Systems, Exton, Pa.). More specifically, in the RBP model, a cannula is placed in the left carotid artery and the side branches are tied off. A physiologic buffer containing the compound (5 micromolar) is perfused at a flow rate of 10 mL/min in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatograph with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., in, Ertl, P., et al., *J. Med. Chem.* 2000, 43, 3714-3717; and Kelder, J., et al., *Pharm. Res.* 1999, 16, 1514-1519.

A similar barrier to the blood-brain barrier is the blood-cerebrospinal fluid barrier. The blood-cerebrospinal fluid barrier creates a barrier or otherwise reduces the amount of toxic or undesirable substances reaching the cerebrospinal fluid, which is mostly located in the ventricular system and the subarachnoid space. To determine whether and to what extent a compound (e.g., a small molecule drug or conjugate) administered to a patient can cross the blood-cerebrospinal fluid barrier, a known amount of the compound can be administered to mice by injection. A few days following administration of the compound, samples of mouse cerebrospinal fluid can be analyzed for the presence and amount of the compound.

The blood-placental barrier protects the developing fetus from most toxicants distributed in the maternal circulation. This barrier consists of several cellular layers between the maternal and fetal circulatory vessels in the placenta. As in the case of the blood-brain barrier, the placental barrier is not totally impenetrable but effectively slows down the diffusion of most toxicants. To determine whether and to what extent a compound (e.g., a small molecule drug or conjugate) administered to a pregnant mammal can cross the blood-placental barrier, a known amount of the compound can be administered to pregnant mice by injection. A few days following administration of the compound, samples of mouse fetal tissue can be analyzed for the presence and amount of the compound.

The blood-milk barrier is similar to the blood-brain barrier in that a biological membrane separates and limits certain substances in the systemic circulation from crossing through. In the case of the blood-milk barrier, the biological membrane prevents certain substances from passing into the mammary glands. To determine whether and to what extent a compound (e.g., a small molecule drug or conjugate) administered to a pregnant mammal can cross the blood-milk barrier, a known amount of the compound can be administered to lactating mice by injection. A few days following administration of the compound, samples of milk from the mammary glands can be analyzed for the presence and amount of the compound.

The blood-testes barrier is comprised sustentacular cells (Sertoli cells) cells which line the male reproductive tract and are joined by tight junctions. To determine whether and to what extent a compound (e.g., a small molecule drug or conjugate) administered to a male mammal can cross the blood-testes barrier, a known amount of the compound can be administered to male mice by injection. A few days following administration of the compound, the mouse's testes can be removed and analyzed for the presence and amount of the compound.

Mucosal barriers represent another biological membrane that typically blocks or reduces undesirable substances from reaching systemic circulation. Administration of a compound to the particular mucosal area of interest and then analyzing a blood sample for the presence and amount of the compound can determine whether and to what extent the compound crosses that particular mucosal area.

With respect to any biological membrane, the water-soluble oligomer-small molecule drug conjugate exhibits a biological membrane crossing rate that is reduced as compared to the biological membrane crossing rate of the small molecule drug not attached to the water-soluble oligomer. Exemplary reductions in biological membrane crossing rates include reductions of: at least about 5%; at least about 10%; at least about 25%; at least about 30%; at least about 40%; at least about 50%; at least about 60%; at least about 70%; at least about 80%; or at least about 90%, when compared to the biological membrane crossing rate of the small molecule drug not attached to the water-soluble oligomer. A preferred reduction in the biological membrane crossing rate for a conjugate is at least about 20%. In some instances, it is preferred that the small molecule drug itself is one that does cross one or more of the biological membranes described herein.

The conjugates exhibiting a reduced biological membrane crossing rate will typically comprise the structure

O-X-D wherein: O corresponds to a water-soluble oligomer, X corresponds to a stable linkage, and D corresponds to the moiety derived from a small molecule drug.

The moiety derived from a small molecule drug is, in one sense, different than the parent small molecule drug in that it is linked, typically through a covalent bond, to an atom that is not associated with the parent small molecule drug. Except for the difference of being linked to another atom, however, the moiety derived from a small molecule drug is essentially the same as the small molecule drug and will have a similar pharmacologic mechanism of action. Thus, a discussion of the small molecule drug serves equally well to describe the moiety derived from a small molecule drug.

The active agents used in the conjugates are small molecule drugs, that is to say, pharmacologically active compounds having a molecular weight of less than about 1000 Daltons. Small molecule drugs, for the purpose of the invention, include oligopeptides, oligonucleotides, and other biomolecules having a molecular weight of less than about 1000 Daltons. Also encompassed in the term "small molecule drug" is any fragment of a peptide, protein or antibody, including native sequences and variants falling within the molecular weight range stated above.

Exemplary molecular weights of small molecule drugs include molecular weights of: less than about 950; less than about 900; less than about 850; less than about 800; less than about 750; less than about 700; less than about 650; less than about 600; less than about 550; less than about 500; less than about 450; less than about 400; less than about 350; and less than about 300.

The small molecule drug used in the invention, if chiral, may be obtained from a racemic mixture, or an optically active form, for example, a single optically active enantiomer, or any combination or ratio of enantiomers. In addition, the small molecule drug may possess one or more geometric isomers. With respect to geometric isomers, a composition can comprise only a single geometric isomer or a mixture of two or more geometric isomers. A small molecule drug for use in the present invention can be in its customary active more, or may possess some degree of modification. For example, a small molecule drug may have a targeting agent, tag, or transporter attached thereto, prior to or after covalent attachment of an oligomer. Alternatively, the small molecule drug may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In some instances, however, it is preferred that the small molecule drug moiety does not include attachment to a lipophilic moiety.

A small molecule for use in coupling to an oligomer of the invention may be any of the following. Suitable agents may be selected from, for example, respiratory drugs, anticonvulsants, muscle relaxants, anti-inflammatories, appetite suppressants, antimigraine agents, muscle contractants, anti-infectives (antibiotics, antivirals, antifungals, vaccines) antiarthritics, antimalarials, antiemetics, bronchodilators, antithrombotic agents, antihypertensives, cardiovascular drugs, antiarrhythmics, antioxicants, anti-asthma agents, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

More particularly, the active agent may fall into one of a number of structural classes, including but not limited to small molecules, oligopeptides, polypeptides or protein mimetics, fragments, or analogues, steroids, nucleotides, oligonucleotides, electrolytes, and the like. Preferably, an active agent for coupling to an oligomer of the invention possesses a free hydroxyl, carboxyl, thio, amino group, or the like (i.e., "handle") suitable for covalent attachment to the oligomer. Alternatively, the drug is modified by introduction of a suitable "handle", preferably by conversion of one of its existing functional groups to a functional group suitable for formation of a stable covalent linkage between the oligomer and the drug. Both approaches are illustrated in the Experimental section.

Specific examples of active agents suitable for covalent attachment to an oligomer of the invention include small molecule mimetics and active fragments (including variants) of the following: aspariginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, collagen, cyclosporin, alpha defensins, beta defensins, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones human growth hormone (hGH), growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau, consensus interferon; interleukins and interleukin receptors such as interleukin-1 receptor, interleukin-2, interluekin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, thymosin alpha 1 IIb/IIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosponates, respiratory syncytial virus antibody, cystic fibrosis transmembrane regulator (CFTR) gene, deoxyreibonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, afeliomomab, basiliximab, daclizumab, infliximab, ibritumomab tiuexetan, mitumomab, muromonab-CD3, iodine 131 tositumomab conjugate, olizumab, rituximab, and trastuzumab (herceptin).

Additional agents suitable for covalent attachment to an oligomer of the invention include but are not limited to amifostine, amiodarone, aminocaproic acid, aminohippurate sodium, aminoglutethimide, aminolevulinic acid, aminosalicylic acid, amsacrine, anagrelide, anastrozole, asparaginase, anthracyclines, bexarotene, bicalutamide, bleomycin, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daunorubicin, deferoxamine, dexamethasone, diclofenac, diethylstilbestrol, docetaxel, doxorubicin, epirubicin, estramustine, etoposide, exemestane, fexofenadine, fludarabine, fludrocortisone, fluorouracil, fluoxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lisinopril, lovothyroxine sodium, lomustine, mechlorethamine, medroxyprogesterone, megestrol, melphalan, mercaptopurine, metaraminol bitartrate, methotrexate, metoclopramide, mexiletine, mitomycin, mitotane, mitoxantrone, naloxone, nicotine, nilutamide, octreotide, oxaliplatin, pamidronate, pentostatin, pilcamycin, porfimer, prednisone, procarbazine, prochlorperazine, ondansetron, raltitrexed, sirolimus, streptozocin, tacrolimus, tamoxifen, temozolomide, teniposide, testosterone, tetrahydrocannabinol, thalidomide, thioguanine, thiotepa, topotecan, tretinoin, valrubicin, vinblastine, vincristine, vindesine, vinorelbine, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

The above exemplary drugs are meant to encompass, where applicable, analogues, agonists, antagonists, inhibitors, isomers, polymorphs, and pharmaceutically acceptable salt forms thereof. Thus, for example, to the extent that an exemplary drug provided above is relatively large and would not be classified as a small molecule drug, the exemplary drug is still listed because an analogue of that large molecule having a similar activity but small size can be used.

Small molecule drugs particularly well suited for the invention are those that can measurably cross a biological membrane. Small molecule drugs exhibiting passage across the dermal barrier are also contemplated. In some instances, the small molecule drug is one, that when administered orally or even parenterally, undesirably crosses a biological barrier to a significant degree. For example, a small molecule drug that undesirably crosses the blood-brain barrier is one that exhibits a brain uptake rate greater than that of atenolol. In this regard, small molecule drugs that have a brain uptake rate ("BUR"), when measured as described herein, of greater than about 15 pmol/gm brain/sec are nonlimiting examples of small molecule drugs that undesirably cross the blood-brain barrier.

Thus, with respect to the blood-brain barrier, small molecule drugs intended for non-central nervous system indications that nonetheless cross the blood-brain barrier are preferred since conjugation of these drugs provides a molecule having less central nervous system side effects. For example, the structurally related nucleotides and nucleosides (e.g., 8-azaguanine, 6-mercaptupurine, azathioprene, thioinosinate, 6-methylthioinosinate, 6-thiouric acid, 6-thioguanine, vidarabine, cladribine, ancitabine, azacytidine, erythro-9-(2-hydroxy-3-nonyl)adenine, fludarabine, gemcitabine, and so forth) are preferred.

With respect to fludarabine, this small molecule drug exhibits about 70% oral bioavailability, and is used for treatment of chronic lymphocytic leukemia, as well as for treatment of hairy cell leukemia, non-Hodgkins lymphoma, and mycosis fungoides. Fludarabine also exhibits central nervous system-related side effects, with severe neurologic effects including blindness, coma and even death. Animal studies in rats and rabbits indicate that the drug may also be teratogenic. Thus, a fludarabine conjugate is expected to be effective in either blocking the penetration of drugs through the blood-brain barrier and/or blood-placenta barrier or at least slowing the crossing rate across these barriers such that adverse side effects of fludarabine are ameliorated.

Another class of small molecule drug that has common central nervous system-related side effects although is typically used for peripheral activities is the small molecule drug class of antihistamines. Structurally, antihistamines as a class are related as aminoalkyl ethers. Such small molecule drugs include diphenhydramine, bromodiphenhydramine, doxylamine, carbinoxamine, clemastine, dimenhydrinate, tripelennamine, pyrilamine, methapyrilene, thonzylamine, pheniramine, chlorpheniramine, dexchlorpheniramine, bromopheniramine, dexbromopheniramine, pyrrobutamine, triprolidine, promethazine, trimeprazine, methdilazine, cyclizine, chlorcyclizine, diphenylpyraline, phenindamine, dimethindene, meclizine, buclizine, antazoline, cyroheptadine, azatadine, terfenadine, fexofenadine, astemizole, cetirizine, azelastine, azatadine, loratadine, and desloratadine.

Still another class of small molecule drug in which a reduction in the blood-brain barrier crossing rate is desired are the opiod antagonists. Opiod antagonists include, naloxone, N-methylnaloxone, 6-amino-14-hydroxy-17-allylnordesomorphine, naltrendol, naltrexone, N-methylnaltrexone, nalbuphine, butorphanol, cyclazocine, pentazocine, nalmephene, naltrendol, naltrindole, nor-binaltorphimine, oxilorphan, 6-amino-6-desoxo-naloxone, pentazocine, levallorphanmethylnaltrexone, buprenorphine, cyclorphan, levalorphan, and nalorphine, as well as those described in U.S. Pat. Nos. 5,159,081, 5,250,542, 5,270,328, and 5,434, 171 and in Knapp et a. "The pharmacology of Opiod Peptides" L. F. Tseng Ed., p. 15, Harwood Academic Publishers, 1995. Generally, however, any member of the oxymorphone chemical class (including the opiod antagonists above, as well as oxymorphone, codeine, oxycodone, morphine, ethylmorphine, diacetylmorphine, hydromorphone, dihydrocodeine, dihydromorphine, and methyldihydromorphine).

Another chemical class of small molecule drugs are the platinum coordination complex-based drugs. These include, for example, cis-platin, hydroplatin, carboplatin, and oxaliplatin.

Another class of small molecule drugs particularly well suited to be conjugated is the steroid class. Preferred steroids have a hydroxyl group in their molecular structure (or an acyl group that can be reduced to form a hydroxyl group). Non-limiting examples of steroids include aldosterone, deoxycorticosterone, fludrocortisone, cortisone, hydrocortisone, prednisolone, prednisone, medrysone, meprednisone, alclometasone, beclomethasone, betamethasone, dexamethasone, diflorasone, flumethasone, methylprednisolone, paramethasone, amcinonide, desonide, fluocinolone, flunisolide, flurandrenolide, triamcinolone, clobetasol, halcinonide, mometasone, clocortolone and desoximetasone.

Fluoroquinolones and related small molecule drugs in this class can be used to form conjugates. Exemplary fluoroquinolones include those ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin and sitafloxacin.

Still another class of drug that is generally used for peripheral indications, some members of which are known to be teratogenic, is the retinoid class of small molecule drugs. The structurally related class of retinoids include, without limitation, retinol, retinal, 3-dehydroretinol, α-carotene, β-carotene, γ-carotene, δ-carotene, crytoxanthin, tretinoin, isotretinoin, etretinate, and eretin. Due to the potential for teratogenicity for this class of small molecule drug (or any class of drug that causes teratogenicity), it is desirable to reduce potential harm to the fetus by eliminating entirely or decreasing the rate of blood-placental barrier crossing of agents suspected of being teratogens.

Additional small molecule drugs for use as part of the conjugates described herein include phenothiazines, dibenzo-diazepines, galactogugues such as metoclopramide, and thiazides. Examples of phenothiazines include prochlorperazine, perphenazine, trifluoroperazine, and fluphenazine. Examples of dibenzo-diazepines include clozapine, olanzapine, and quetiapine. Other small molecule drugs include amlodipine, nifedipine, nimodipine, nimodipine, 5-hydroxytryptophan, retinoic acid, and isotretinoin. Another preferred drug is nevirapine, which readily crosses the placental barrier.

Additional small molecule drugs suitable for use in the invention can be found in, for example, in "The Merck Index, 13th Edition, Merck & CO., Inc. (2001); "The AHFS Drug Handbook, 2nd Edition", American Society of Health System Pharmacists and Lippincott, Williams and Wilkins; "The Physicians Desk Reference", Thomson Healthcare Inc., 2003; and "Remington: The Science and Practice of Pharmacy", 19th Edition, 1995.

By modifying the small drug molecule as provided above with covalent attachment of a water-soluble oligomer obtained from a monodisperse or bimodal oligomer composition, significant changes in the small molecule drug's transport and pharmacological properties can result. The use of a water-soluble oligomer from a monodisperse or bimodal oligomer composition allows for tailoring of drug properties, since the resultant conjugates form a well-defined composition rather than a distribution of a series of small molecule drug-oligomer conjugate species having a distribution of monomer subunits (and therefore molecular weights). As previously stated, the addition or deletion of as little as one monomer is observed to have a measurable effect on the properties of the resulting conjugate. Screening of a matrix of discrete oligomers of different sizes (from 1 to 30 monomer subunits) can be conducted in a reasonable amount of time, and allows for the tailoring of customizing of conjugates having optimized properties.

The oligomers, when attached to the small molecule drug, provide differences in properties compared to the parent small drug molecule. The use of small oligomers (in comparison to the 5K to 60K polymer chains that are typically attached to proteins) also increases the likelihood of the drug maintaining at least a degree, and preferably a significant degree, of its bioactivity. This feature is demonstrated in Table VI (Example 10), which provides bioactivity ($EC_{50}$) data for exemplary conjugates of the invention. The illustrative PEG oligomer-naloxone/naloxol conjugates possess bioactivities ranging from about 5% to about 35% of the unmodified parent drug, further demonstrating the beneficial features of the compounds of the invention.

The oligomer typically comprises two or more monomers serially attached to form a chain of monomers. The oligomer can be formed from a single monomer type (i.e., is homo-oligomeric) or two or three monomer types (i.e., is co-oligomeric). Preferably, each oligomer is a co-oligomer of two monomers or, more preferably, is a homo-oligomer. The monomer(s) employed result in an oligomer that is water soluble as defined herein, that is, >95% water soluble, preferably >99% water soluble, in water at room temperature at physiological pH (about 7.2-7.6).

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; α-hydroxy acid, such as lactic acid or glycolic acid; phosphazene, oxazoline, amino acids, carbohydrates such as monosaccharides, saccharide or mannitol; and N-acryloylmorpholine. Preferred monomer types include alkylene oxide, olefinic alcohol, hydroxyalkyl methacrylamide or methacrylate, N-acryloylmorpholine, and α-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble oligomer ("O" in the conjugate formula O-X-D) can have any of a number of different geometries. For example, "O" (in the formula O—X-D) can be linear, branched, or forked. Most typically, the water-soluble oligomer is linear or is branched, for example, having one branch point. Although much of the discussion herein is focused upon poly(ethylene oxide) as an illustrative oligomer, the discussion and structures presented herein can be readily extended to encompass any of the water-soluble oligomers described above.

The molecular weight of the water-soluble oligomer, excluding the linker portion, is generally relatively low. Exemplary values of the molecular weight of the water-soluble polymer include: below about 1500; below about 1400; below about 1300; below about 1200; below about 1100; below about 1000; below about 900; below about 800; below about 700; below about 600; below about 500; below about 400; below about 300; below about 200; and below about 100 Daltons.

Exemplary ranges of molecular weights of the water-soluble oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble oligomer falls within one or more of the following ranges: between about 1 and about 30 (inclusive); between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers in series. In yet further embodiments, the oligomer (and the corresponding conjugate) possesses 21, 22, 23, 24, 25, 26, 27, 28, 29 or 30 monomers in series.

When the water-soluble oligomer has 1, 2, 3, 4, 5, 6, 7, 8, 9, or 10 monomers, these values correspond to a methoxy end-capped oligo(ethylene oxide) having a molecular weights of 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to 515, 559, 603, 647, and 691 Daltons, respectively.

In those instances where a bimodal oligomer is employed, the oligomer will possess a bimodal distribution centering around any two of the above numbers of monomers. Ideally, the polydispersity index of each peak in the bimodal distribution, Mw/Mn, is 1.01 or less, and even more preferably, is 1.001 or less, and even more preferably is 1.0005 or less. Most preferably, each peak possesses a MW/Mn value of 1.0000.

For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-4, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In addition, the oligomer of the invention can be trimodal or even tetramodal, possessing a range of monomers units as previously described. Oligomer compositions possessing a well-defined mixture of oligomers (i.e., being bimodal, trimodal, tetramodal, etc.) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range. As can be seen from FIG. 10, commercially available PEGs are typically polydisperse mixtures, even for low molecular weight materials. The methoxy-PEG sample shown was analyzed by mass spectrometry, and although labeled as methoxy-PEG-350, the reagent was found to contain 9 different PEG oligomer components, each differing in the number of monomer subunits. For the purposes of the present invention, that is to say, to prepare conjugates having the features described herein, polydisperse polymers are not particularly preferred, since small changes in the number of monomers have been discovered to have a profound effect on the properties of the resulting conjugates. Such effects would likely be dampened or even undetectable in a conjugate mixture prepared using a polydisperse oligomer. Moreover, commercial batches of polydisperse polymers (or oligomers) are often highly variable in their composition, and for this reason, are not particularly preferred for the present application, where batch-to-batch uniformity is a desirable feature for an oligomer as described herein.

As described above, the water-soluble oligomer is obtained from a composition that is preferably unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. For example, oligoethylene glycols of the invention can be prepared as described, e.g., in Chen Y., Baker, G. L., J. Org. Chem., 6870-6873 (1999), or in WO 02/098949 A1. Alternatively, such oligomers can be prepared as described herein in Example 9.

As described above, one aspect of the invention is an improved method of preparing a monodisperse oligomers such as an oligo(ethylene oxide). These oligomers can be used in any of a variety of applications, including but not limited to preparing a small molecule drug-water-soluble oligomer conjugate having the beneficial properties set forth above.

In order to provide the desired monodisperse oligomers, a new approach was used. It was discovered that halo-terminated oligomer reagents are more reactive and produce higher yields of monofunctional products in comparison to previously described reagents.

Thus, the present invention also includes a method for preparing monodisperse oligomer compositions. The method involves reacting a halo-terminated oligomer such as an oligo(ethylene oxide) having (m) monomers with a hydroxyl-terminated oligo(ethylene oxide) having (n) monomers. Generally, the halo group on the halo terminated oligoethylene glycol is a chloro, bromo or iodo group. Preferably, however, the halo group is bromo. The reaction is carried out under conditions effective to displace the halo group from the halo-terminated oligomer to thereby form an oligo(ethylene oxide) having (m)+(n) monomer subunits (OEG$_{m+n}$), where (m) and (n) each independently range from 1-10. That is to say, each of (m) and (n) is independently 1, 2, 3, 4, 5, 6, 7, 8, 9, or 10. Preferably, (m) and (n) each independently range from 1 to about 6. In selected embodiments, (m) is 1, 2, or 3 and (n) ranges from 1-6. In other instances, (m) is 1, 2, or 3, and (n) ranges from 2-6. Typically, the reaction is carried out in the presence of a strong base effective to convert the hydroxyl group of the hydroxyl-terminated oligoethylene oxide into the corresponding alkoxide species. Suitable bases include sodium, potassium, sodium hydride, potassium hydride, sodium methoxide, potassium methoxide, sodium tert-butoxide, and potassium tert-butoxide. In a preferred embodiment, the halo-terminated oligoethylene glycol possesses an end-capping group such as methoxy or ethoxy.

Representative hydroxy-terminated oligo(ethylene glycol)s correspond to the structure HO—(CH$_2$CH$_2$O)$_n$—H, where (n) is as described above. The method then preferably includes the step of converting the terminal hydroxyl group of OEG$_{m+n}$ into a halo group, —X, to form OEG$_{m+n}$-X. The above steps are then repeated until a unimolecular oligomer having the desired number of subunits is obtained.

An illustrative reaction scheme is as follows.

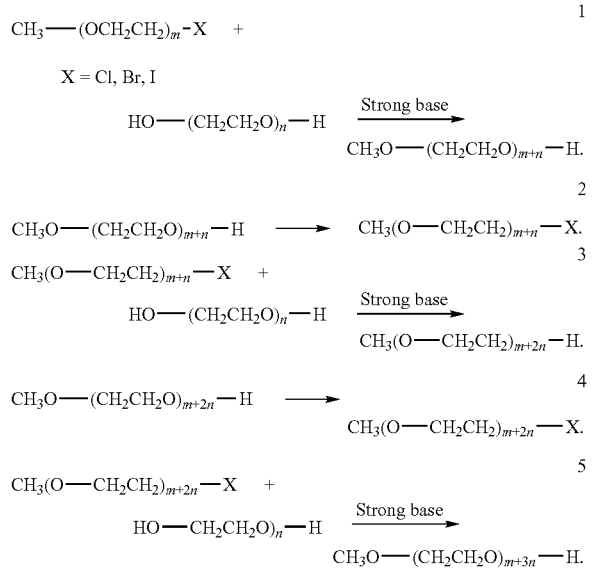

As shown, the method involves the coupling of two unimolecular oligomer species by employing a substitution reaction where a halide on one oligomer, preferably an oligomeric ethylene oxide, and even more preferably, a halo-derivatized oligoethylene oxide methyl ether, is reacted with an oligoethylene glycol-alkoxide to generate the corresponding oligomer (see reaction 1 above).

The alkoxide is typically generated from the corresponding oligoethylene oxide by converting the terminal hydroxyl to the corresponding alkoxide in the presence of a strong base. The reaction is generally carried out in an organic solvent such as tetrahydrofuran ("THF") at temperatures ranging from about 0° C. to about 80° C. Reaction times typically range from about 10 minutes to about 48 hours. The resultant product, in the exemplary reaction above, an end-capped oligoethylene oxide, contains a sum of the number of monomers of the halo-derivatized oligomer and the number of monomers in the oligoethylene glycol alkoxide [(m)+(n)]. Yields typically range from about 25% to about 75% for the purified coupled product, with yields most typically ranging from about 30 to about 60%.

In the above example, the hydroxyl terminus in the product from reaction 1 is then activated, if necessary, for coupling to a small molecule. Alternatively, if desired, the hydroxyl terminus in the exemplary product shown above [in the above example having (m)+(n) subunits), is then converted to a halide, preferably a bromide. Conversion of an alcohol to an alkyl halide can by effected directly, or through an intermediate such as a sulfonate or haloformate. Conditions and reagents suitable for effecting this transformation are found, for example, in Larock, R., "*Comprehensive Organic Transformations*", VCH, 1994, pages 353 to 363.

One preferred method is that set forth in Example 11. The stepwise addition of the oligoethylene oxide halide to an oligoethylene oxide is then repeated as described above, to form an oligoethylene oxide having (m)+2(n) monomers, and so-forth. In this manner, discrete oligoethylene oxide subunits are then added in a controlled, stepwise fashion to the existing monomeric (unimolecular) oligomeric ethylene oxide product, to ensure preparation of a well-defined oligomer having an exact number of subunits.

Commonly available are unimolecular oligoethylene glycols having from about 1-3 monomer subunits (Sigma-Aldrich). Use of a halo-substituted oligomeric ethylene glycol reactant represents an improvement over existing methods, e.g., employing the mesylate, since the approach provided herein results in improved yields, shorter reaction times and milder reaction conditions due to the higher reactivity of the halide, and in particular, the bromo-substituted oligoethylene glycol reagent. Oligomers thus prepared are typically purified prior to further use, for example, by one or more of the following methods: chromatography such as HPLC, ion exchange chromatography, column chromatography, precipitation, or recrystallization. Purity is then confirmed by any of a number of analytical techniques, such as NMR, GPC, and FTIR. Products thus formed are then suitable for further use.

The linker or linkage of the invention may be a single atom, such as an oxygen or a sulfur, two atoms, or a number of atoms. A linker is typically but is not necessarily linear in nature. The linkage, "X" (in the O-X-D formula), is hydrolytically stable, and is preferably also enzymatically stable. Preferably, the linkage "X" is one having a chain length of less than about 12 atoms, and preferably less than about 10 atoms, and even more preferably less than about 8 atoms or even more preferably less than about 5 atoms, whereby length is meant the number of atoms in a single chain, not counting substituents. For instance, a urea linkage such as this, R$_{oligomer}$—NH—(C=O)—NH—R'$_{drug}$, is considered to have a chain length of 3 atoms (—NH—C(O)—NH—). In selected embodiments, the linkage does not comprise further spacer groups. Small linkages are preferred and lend themselves to the nature of the present invention, since small linkages such as these are less likely to dominate or overshadow the effect of an addition of one or a small number of monomer subunits on the difference in transport properties of the conjugates of the invention.

In some instances, the linker "X" is hydrolytically stable and comprises an ether, amide, urethane, amine, thioether, urea, or a carbon-carbon bond. Functional groups such as those discussed below, and illustrated in the working examples, are typically used for forming the linkages. The linkage may less preferably also comprise (or be adjacent to or flanked by) spacer groups, as described further below. Spacers are most useful in instances where the bioactivity of the conjugate is significantly reduced due to the positioning of the oligomer on the parent drug.

More specifically, in selected embodiments, a linker of the invention, L, may be any of the following: —O—, —NH—, —S—, —C(O)—, C(O)—NH, NH—C(O)—NH, O—C (O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C (O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C (O)—, —CH$_2$—CH$_2$—CH$_2$—C(O)—NH—CH$_2$—CH$_2$—NH—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl.

For purposes of the present invention, however, a series of atoms is not considered as a linkage when the series of atoms is immediately adjacent to an oligomer segment, and the series of atoms is but another monomer such that the proposed linkage would represent a mere extension of the oligomer chain.

The linkage "X" between the oligomer and the small molecule is typically formed by reaction of a functional group on a terminus of the oligomer with a corresponding functional group within the small molecule drug. Illustrative reactions are described briefly below. For example, an amino group on an oligomer, "O," may be reacted with a carboxylic acid or an activated carboxylic acid derivative on the small molecule, or vice versa, to produce an amide linkage. Alternatively, reaction of an amine on an oligomer with an activated carbonate (e.g. succinimidyl or benzotriazyl carbonate) on the drug, or vice versa, forms a carbamate linkage. Reaction of an amine on an oligomer with an isocyanate (R—N=C=O) on a drug, or vice versa, forms a urea linkage (R—NH—(C=O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

A particularly preferred oligomer is an oligomer bearing an aldehyde functional group. In this regard, the oligomer will have the following structure: CH$_3$O—(CH$_2$—CH$_2$—O)$_n$—(CH$_2$)$_p$—C(O)H, wherein (n) is one of 1, 2, 3, 4, 5, 6, 7, 8, 9 and (p) is one of 1, 2, 3, 4, 5, 6 and 7). Preferred (n) values include 3, 5 and 7 and preferred (p) values 2, 3 and 4. In addition, the carbon atom alpha to the —C(O)H moiety can optionally be substituted with alkyl. The oligomer reagent is preferably provided as a monodisperse composition.

Typically, the terminus of the oligomer not bearing a functional group is capped to render it unreactive. When the oligomer does includes a further functional group at a terminus other than that intended for formation of a conjugate, that group is either selected such that it is unreactive under the conditions of formation of the linkage "X," or it is protected during the formation of the linkage "X."

As stated above, the oligomer includes a functional group for forming a small molecule conjugate having the properties described herein. The functional group typically comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—NHNH$_2$), hydrazide (—C(O)NHNH$_2$), and thiol. Preferred nucleophiles include amine, hydrazine, hydrazide, and thiol, particularly amine. Most small molecule drugs for covalent attachment to an oligomer will possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, etc., as well as hydrates or protected derivatives of any of the above moieties (e.g. aldehyde hydrate, hemiacetal, acetal, ketone hydrate, hemiketal, ketal, thioketal, thioacetal). Another useful conjugation reagent is 2-thiazolidine thione.

As noted above, an "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —$(CH_2)_{2-3}C(=O)O$-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g. hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. As mentioned above, most preferred are conjugates having a hydrolytically stable linkage between the oligomer and the drug. Carbonates, including succinimidyl, imidazolyl, and benzotriazole carbonates, react with amino groups to form carbamates. Isocyanates (R—N=C=O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e. aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups which can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

For instance, the preparation of an exemplary oligomeric conjugate of retinoic acid is described in detail in Example 1. Briefly, the small molecule, retinoic acid, which contains a reactive carboxyl group, is coupled to an amino-activated oligomeric ethylene glycol, to provide a conjugate having an amide group covalently linking the small molecule to the oligomer. The covalent attachment of each a PEG 3-mer (meaning an oligomeric ethylene glycol having 3 ethylene glycol monomer subunits), a PEG 7-mer, and a PEG 11-mer to retinoic acid is described.

Further, the preparation of an oligomer-conjugate of naloxone is described in Example 4. In this representative synthesis, following protection of an aromatic hydroxyl group, a keto group in naloxone is reduced to the corresponding hydroxyl, which is then coupled to an oligomeric ethylene glycol halide to result in an ether (—O—) linked small molecule conjugate. Interestingly, in this example, reduction of the hydroxyl group in naloxone resulted in formation of two stereoisomers differing in the orientation of the hydroxyl group. The corresponding oligomeric conjugates were prepared and separated, and shown to have somewhat different characteristics, to be discussed in greater detail below. This represents another feature of the invention, that is, the preparation/isolation of single isomers of oligomer-small molecule conjugates, and uses thereof.

The conjugates of the invention exhibit a reduced biological barrier crossing rate as previously described. Moreover, the conjugates maintain at least about 5%, 10%, 20%, 30%, 40%, 50%, 60%, 70%, or more of the bioactivity of the unmodified parent small molecule drug. For a given small molecule drug having more than one reactive site suitable for modification, it may be necessary to carry out molecular modeling, or in vivo or in vitro biological activity assays to assess the biological activity of the resulting conjugate and determine the site most suitable for covalent attachment of an oligomer. See for example the illustrative bioactivity data in Table VI for various oligomer conjugates of naloxone and derivatized naloxone, 6-$NH_2$-naloxone and 6-OH-naloxol. In this investigation, variables included the site of chemical modification on the parent drug, type of covalent linkage, stereochemistry, and size of oligomer covalently attached to the drug moiety. As can be seen from the data, the bioactivities of the conjugates ranged from about 5% to about 35% of the bioactivity of the parent drug.

It has been discovered that stable covalent attachment of small, water-soluble oligomers to orally bioavailable small molecule drugs is effective to significantly alter the properties of these molecules, thereby making them more clinically effective. More specifically, covalent attachment of monodisperse oligomers such as oligoethylene oxide is effective to reduce, or in some cases, eliminate, a drug's transport across the blood brain barrier, which then translates into a significant reduction in central nervous system-related side effects. The selection of an optimally sized oligomer is typically conducted as follows.

First, an oligomer obtained from a monodisperse or bimodal water soluble oligomer is conjugated to a small molecule drug. Preferably, the drug is orally bioavailable, and on its own, exhibits a biological membrane crossing rate. Next, the ability of the conjugate to cross the biological membrane is determined using an appropriate model and compared to that of the unmodified parent drug. If the results are favorable, that is to say, if, for example, the rate of crossing is significantly reduced, then the bioactivity of conjugate is further evaluated. A beneficial conjugate in accordance with the invention is bioactive, since the linkage is hydrolytically stable and does not result in release of unmodified drug upon administration. Thus, the drug in conjugated form should be bioactive, and preferably, maintains a significant degree of bioactivity relative to the parent drug, i.e., greater than about 30% of the bioactivity of the parent drug, or even more preferably, greater than about 50% of the bioactivity of the parent drug.

Then, the above steps are repeated using oligomers of the same monomer type but having a different number of subunits.

Because the gastro-intestinal tract ("GIT") limits the transport of food and drugs from the digestive lumen in to blood and the lymph, the GIT represents another barrier for which the conjugate must be tested. The GIT barrier, however, represents a barrier that must not block the conjugates when the conjugate is intended for oral administration for systemic delivery. The GIT barrier consists of continuous layers of intestinal cells joined by tight junctions in the intestinal epithelia.

For each conjugate whose ability to cross a biological membrane is reduced in comparison to the non-conjugated small molecule drug, its oral bioavailability is then assessed.

Based upon these results, that is to say, based upon the sequential addition of increasing numbers of discrete monomers to a given small molecule at a given position or location within the small molecule, it is possible to determine the size of the oligomer most effective in providing a conjugate having an optimal balance between reduction in biological membrane crossing, oral bioavailability, and bioactivity. The small size of the oligomers makes such screenings feasible, and allows one to effectively tailor the properties of the resulting conjugate. By making small, incremental changes in oligomer size, and utilizing an experimental design approach, one can effectively identify a conjugate having a favorable balance of reduction in biological membrane crossing rate, bioactivity, and oral bioavailability. In some instances, attachment of an oligomer as described herein is effective to actually increase oral bioavailability of the drug.

For example, one of ordinary skill in the art, using routine experimentation, can determine a best suited molecular size and linkage for improving oral bioavailability by first preparing a series of oligomers with different weights and functional groups and then obtaining the necessary clearance profiles by administering the conjugates to a patient and taking periodic blood and/or urine sampling. Once a series of clearance profiles have been obtained for each tested conjugate, a suitable conjugate can be identified.

Animal models (rodents and dogs) can also be used to study oral drug transport. In addition, non-in vivo methods include rodent everted gut excised tissue and Caco-2 cell monolayer tissue-culture models. These models are useful in predicting oral drug bioavailability.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder, Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The conjugate can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The invention also provides a method for administering a conjugate as provided herein to a patient suffering from a condition that is responsive to treatment with the conjugate. The method comprises administering, generally orally, a therapeutically effective amount of the conjugate (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering the conjugates of the present invention is that a reduction in first pass metabolism may be achieved relative to the parent drug. See for example the supporting results in Example 8. Such a result is advantageous for many orally administered drugs that are substantially metabolized by passage through the gut. In this way, clearance of the conjugate can be modulated by selecting the oligomer molecular size, linkage, and position of covalent attachment providing the desired clearance properties. One of ordinary skill in the art can determine the ideal molecular size of the oligomer based upon the teachings herein. All articles, books, patents, patent publications and other publications referenced herein are incorporated by reference in their entireties. Preferred reductions in first pass metabolism for a conjugate as compared to the corresponding nonconjugated small drug molecule include: at least about 10%, at least about 20%, at least about 30; at least about 40; at least about 50%; at least about 60%, at least about 70%, at least about 80% and at least about 90%.

Thus, the invention provides a method for reducing the metabolism of an active agent. The method comprises the steps of: providing monodisperse or bimodal conjugates, each conjugate comprised of a moiety derived from a small molecule drug covalently attached by a stable linkage to a water-soluble oligomer, wherein said conjugate exhibits a reduced rate of metabolism as compared to the rate of metabolism of the small molecule drug not attached to the water-soluble oligomer; and administering the conjugate to a patient. Typically, administration is carried out via one type of administration selected from the group consisting of oral administration, transdermal administration, buccal administration, transmucosal administration, vaginal administration, rectal administration, parenteral administration, and pulmonary administration.

Although useful in reducing many types of metabolism (including both Phase I and Phase II metabolism) can be reduced, the conjugates are particularly useful when the small molecule drug is metabolized by a hepatic enzyme (e.g., one or more of the cytochrome P450 isoforms) and/or by one or more intestinal enzymes.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

All chemical reagents referred to in the appended examples are commercially available unless otherwise indicated. The preparation of illustrative unimolecular PEG-mers is described in Example 9. All oligo(ethylene glycol) methyl ethers employed in the Examples below were monodisperse and chromatographically pure, as determined by reverse phase chromatography.

All $^1$H NMR (nuclear magnetic resonance) data was generated by a 300 MHz NMR spectrometer manufactured by Bruker. A list of certain compounds as well as the source of the compounds is provided below.

2-Bromoethyl methyl ether, 92%, Aldrich;
1-Bromo-2-(2-methoxyethoxy)ethane, 90%, Aldrich;
$CH_3(OCH_2CH_2)_3Br$ was prepared from $CH_3(OCH_2CH_2)_3OH$;
Tri(ethylene glycol) monomethyl ether, 95%, Aldrich;
Di(ethylene glycol), 99%, Aldrich;
Tri(ethylene glycol), 99%, Aldrich;
Tetra(ethylene glycol), 99%, Aldrich;
Penta(ethylene glycol), 98%, Aldrich;
Hexa(ethylene glycol), 97%, Aldrich;
Sodium hydride, 95% dry powder, Aldrich;
Methansulfonyl chloride, 99%, ACE;
Tetrabutyl ammonium bromide, Sigma Example 1

Synthesis of $CH_3(OCH_2CH_2)_3$—NH-13-cis-Retinamide (PEG$_3$-13-cis-RA)

PEG$_3$-13-cis-RA was prepared. The overview of the synthesis is provided below.

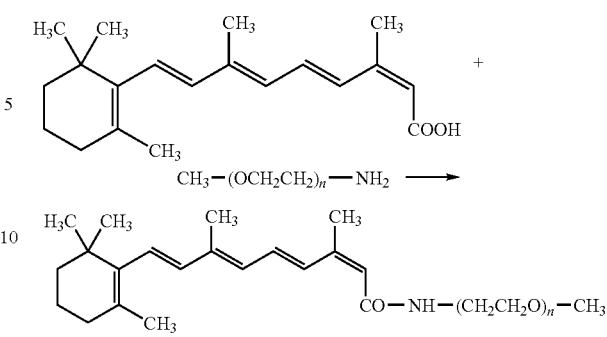

0.1085 grams of $CH_3(OCH_2CH_2)_3$—$NH_2$ (0.6656 mmoles), 0.044 grams of 1-hydroxybenzyltriazole ("HOBT," 0.3328 mmoles), and 0.200 g of 13-cis-retinoic acid ("13-cis-RA," 0.6656 mmoles) were dissolved in 10 mL of benzene. To this solution was added 0.192 grams of 1,3-dicyclohexylcarbodiimide ("DCC," 0.9318 mmoles) and the reaction mixture was stirred overnight at room temperature. The reaction mixture was filtered and the solvent was removed using rotary evaporation. The crude product was further dried under vacuum, dissolved in 20 mL of dichloromethane, and the organic phase was washed twice with 15 mL of deionized water. The organic phase was dried over $Na_2SO_4$, filtered, and the solvent removed by rotary evaporation. To the recovered product was added 2 drops of dichloromethane containing 50 ppm butylated hydroxytoluene and the product was dried under vacuum. Yield 0.335 g. $^1$H NMR (DMSO): δ 1.02 (singlet, 2CH$_3$), 1.67 (singlet, CH$_3$), 3.5 (broad multiplet, PEG), 6.20 (m, 3H).

Example 2

Synthesis of $CH_3$—$(OCH_2CH_2)_7$—NH-13-cis-Retinamide (PEG$_7$-13-cis-RA)

0.2257 grams of $CH_3(OCH_2CH_2)_7$—$NH_2$ (0.6656 mmoles), 0.044 grams of 1-hydroxybenzyltriazole (0.3328 mmoles), and 0.200 grams of 13-cis-retinoic acid (0.6656 mmoles) were dissolved in 10 mL of benzene. To this solution was added 0.192 g 1,3-dicyclohexylcarbodiimide (0.9318 mmoles) and the resulting reaction mixture was stirred overnight at room temperature. The reaction mixture was filtered, the solvent removed using rotary evaporation, and the product dried under vacuum. The product was dissolved in 20 mL dichloromethane and the solution was washed twice with 15 mL deionized water. The organic phase was dried over $Na_2SO_4$, filtered, and the solvent removed using rotary evaporation. To the recovered product was added 2 drops of dichloromethane containing 50 ppm butylated hydroxytoluene, and the product was dried under vacuum. Yield 0.426 g. $^1$H NMR (DMSO): δ 1.01 (s, 2CH$_3$), 1.68 (s, CH$_3$), 3.5 (br m, PEG), 6.20 (m, 3H).

$CH_3$—$(OCH_2CH_2)_5$—NH-13-cis-retinamide ("PEG$_5$-13-cis-RA") was similarly prepared using this procedure except that $CH_3(OCH_2CH_2)_5$—$NH_2$ ("mPEG$_5$-$NH_2$") was used in place of $CH_3(OCH_2CH_2)_7$—$NH_2$.

Example 3

Synthesis of $CH_3$—$(OCH_2CH_2)_{11}$—NH-13-cis-Retinamide (PEG$_{11}$-13-cis-RA)

0.349 grams of $CH_3(OCH_2CH_2)_{11}$—$NH_2$ (0.6789 mmoles), 0.044 grams of 1-hydroxybenzyltriazole (0.3328 mmoles), and 0.204 grams of 13-cis-retinoic acid (0.6789 mmoles) was dissolved in 10 mL of benzene. To this solution was added 0.192 g 1,3-dicyclohexylcarbodiimide (0.9318 mmoles) and the reaction mixture was stirred overnight at room temperature. The reaction mixture was filtered and the solvent distilled off using rotary evaporation. The product was dried under vacuum and dissolved in 20 mL dichloromethane. The solution was washed twice with 15 mL of deionized water and the organic phase dried over $Na_2SO_4$. The solution was filtered and the solvent was distilled off by rotary evaporation. To the recovered product was added 2 drops of dichloromethane containing 50 ppm butylated hydroxytoluene, and the product was dried under vacuum. Yield 0.541 g. $^1$H NMR (DMSO): δ 1.01 (s, $2CH_3$), 1.68 (s, $CH_3$), 3.5 (br m, PEG), 6.20 (m, 3H).

Example 4

Synthesis of $PEG_3$-3-naloxol

The structure of the naloxol, an exemplary small molecule drug, is shown below.

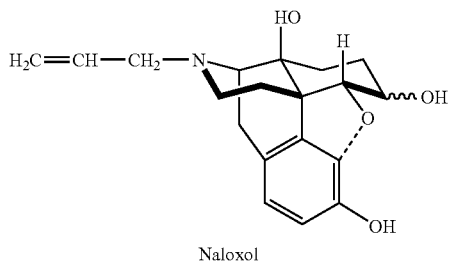

Naloxol

This molecule was prepared (having a protected hydroxyl group) as part of a larger synthetic scheme as described in Example 5.

Example 5

Synthesis of α,β-6-$CH_3$—$(OCH_2CH_2)_1$-naloxol (α,β-$PEG_1$-Nal)

α,β-$PEG_1$-naloxol was prepared. The overview of the synthesis is provided below.

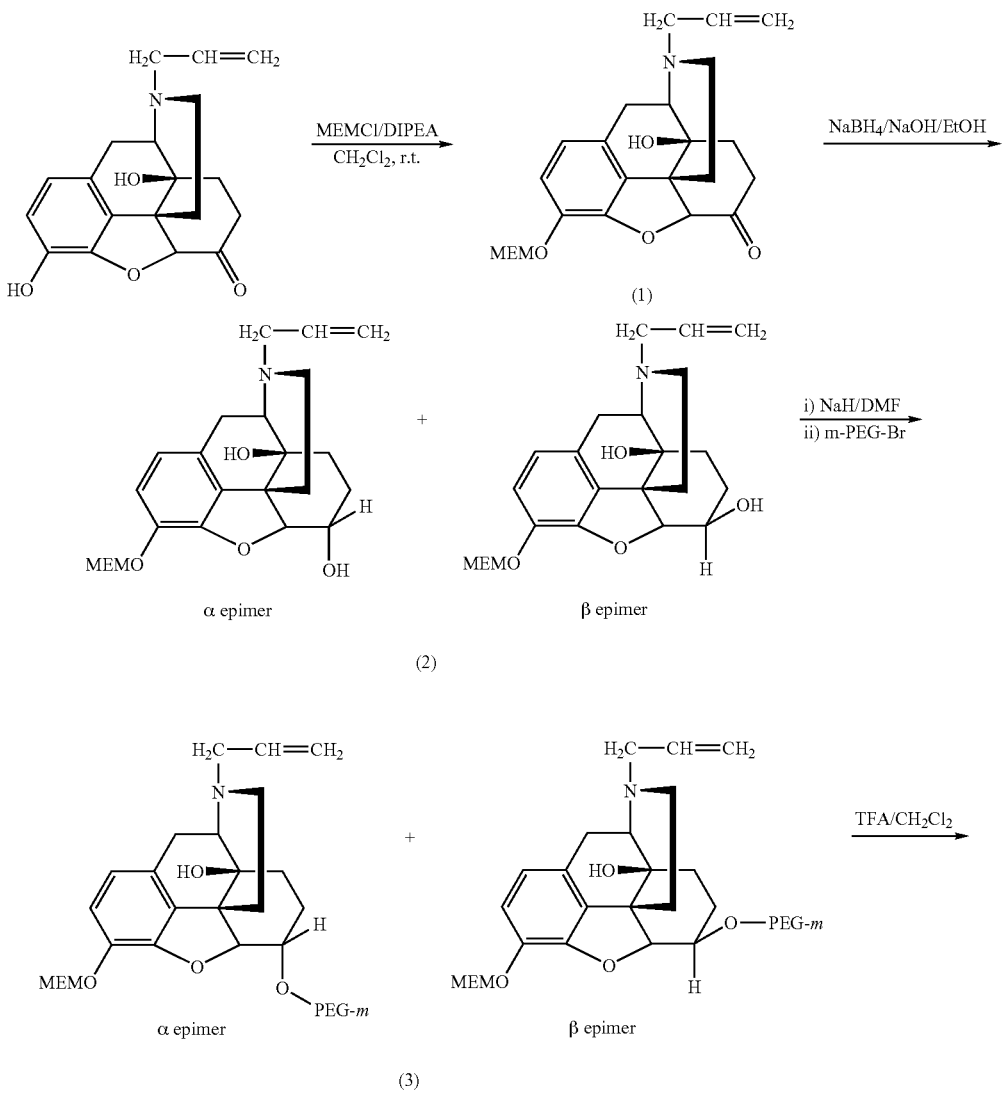

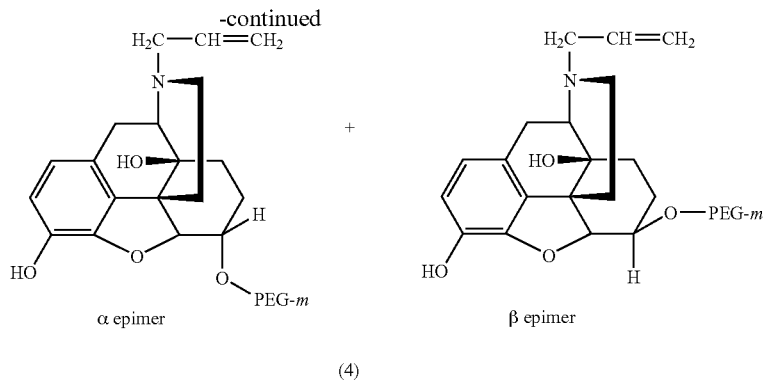

α epimer                    β epimer (4)

5.A. Synthesis of 3-MEM-naloxone

Diisopropylethylamine (390 mg, 3.0 mmole) was added to a solution of naloxone.HCl.2H$_2$O (200 mg, 0.50 mmole) in CH$_2$Cl$_2$ (10 mL) with stirring. Methoxyethyl chloride ("MEMCl," 250 mg, 2.0 mmole) was then added dropwise to the above solution. The solution was stirred at room temperature under N$_2$ overnight.

The crude product was analyzed by HPLC, which indicated that 3-MEM-O-naloxone (1) was formed in 97% yield. Solvents were removed by rotary evaporation to yield a sticky oil.

5.B. Synthesis of α and β Epimer Mixture of 3-MEM-naloxol (2)

3 mL of 0.2 N NaOH was added to a solution of 3-MEM-naloxone (1) (obtained from 5.A. above, and used without further purification) in 5 mL of ethanol. To this was added a solution of NaBH$_4$ (76 mg, 2.0 mmole) in water (1 mL) dropwise. The resulting solution was stirred at room temperature for 5 hours. The ethanol was removed by rotary evaporation followed by addition of a solution of 0.1 N HCl solution to destroy excess NaBH$_4$ and adjust the pH to a value of 1. The solution was washed with CHCl$_3$ to remove excess methoxyethyl chloride and its derivatives (3×50 mL), followed by addition of K$_2$CO$_3$ to raise the pH of the solution to 8.0. The product was then extracted with CHCl$_3$ (3×50 mL) and dried over Na$_2$SO$_4$. The solvent was removed by evaporation to yield a colorless sticky solid (192 mg, 0.46 mmole, 92% isolated yield based on naloxone.HCl.2H$_2$O).

HPLC indicated that the product was an α and β epimer mixture of 3-MEM-naloxol (2).

5.C. Synthesis of α and β Epimer Mixture of 6-CH$_3$—OCH$_2$CH$_2$—O-3-MEM-naloxol (3a)

NaH (60% in mineral oil, 55 mg, 1.38 mmole) was added into a solution of 6-hydroxyl-3-MEM-naloxol (2) (192 mg, 0.46 mmole) in dimethylformamide ("DMF," 6 mL). The mixture was stirred at room temperature under N$_2$ for 15 minutes, followed by addition of 2-bromoethyl methyl ether (320 mg, 2.30 mmole) in DMF (1 mL). The solution was then stirred at room temperature under N$_2$ for 3 hours.

HPLC analysis revealed formation of a mixture of α- and β-6-CH$_3$—OCH$_2$CH$_2$—O-3-MEM-naloxol (3) in about 88% yield. DMF was removed by a rotary evaporation to yield a sticky white solid. The product was used for subsequent transformation without further purification.

5.D. Synthesis of α and β Epimer Mixture of 6-CH$_3$—OCH$_2$CH$_2$-naloxol (4)

Crude α- and β-6-CH$_3$—OCH$_2$CH$_2$—O-3-MEM-naloxol (3) was dissolved in 5 mL of CH$_2$Cl$_2$ to form a cloudy solution, to which was added 5 mL of trifluoroacetic acid ("TFA"). The resultant solution was stirred at room temperature for 4 hours. The reaction was determined to be complete based upon HPLC assay. CH$_2$Cl$_2$ was removed by a rotary evaporator, followed by addition of 10 mL of water. To this solution was added sufficient K$_2$CO$_3$ to destroy excess TFA and to adjust the pH to 8. The solution was then extracted with CHCl$_3$ (3×50 mL), and the extracts were combined and further extracted with 0.1 N HCl solution (3×50 mL). The pH of the recovered water phase was adjusted to a pH of 8 by addition of K$_2$CO$_3$, followed by further extraction with CHCl$_3$ (3×50 mL). The combined organic layer was then dried with Na$_2$SO$_4$. The solvents were removed to yield a colorless sticky solid.

The solid was purified by passage two times through a silica gel column (2 cm×30 cm) using CHCl$_3$/CH$_3$OH (30:1) as the eluent to yield a sticky solid. The purified product was determined by $^1$H NMR to be a mixture of α- and β epimers of 6-CH$_3$—OCH$_2$CH$_2$-naloxol (4) containing ca. 30% α epimer and ca. 70% β epimer [100 mg, 0.26 mmole, 56% isolated yield based on 6-hydroxyl-3-MEM-naloxol (2)].

$^1$H NMR (δ, ppm, CDCl$_3$): 6.50-6.73 (2H, multiplet, aromatic proton of naloxol), 5.78 (1H, multiplet, olefinic proton of naloxone), 5.17 (2H, multiplet, olefinic protons of naloxol), 4.73 (1H, doublet, C$_5$ proton of α naloxol), 4.57 (1H, doublet, C$_5$ proton of β naloxol), 3.91 (1H, multiplet, C$_6$ proton of α naloxol), 3.51-3.75 (4H, multiplet, PEG), 3.39 (3H, singlet, methoxy protons of PEG, α epimer), 3.36 (3H, singlet, methoxy protons of PEG, β epimer), 3.23 (1H, multiplet, C$_6$ proton of β naloxol), 1.46-3.22 (14H, multiplet, protons of naloxol).

Example 6

Synthesis of 6-CH$_3$—(OCH$_2$C$_2$)$_3$-Naloxol (α,β-PEG$_3$-Nal)

6.A. Synthesis of an α and β Epimer Mixture of 6-CH$_3$—(OCH$_2$CH$_2$)$_3$—O-3-MEM-naloxol NaH (60% in mineral oil, 38 mg, 0.94 mmole) was added to a solution of 3-MEM-naloxol [98 mg, 0.24 mmole, from Example 5 and shown as (2) in the schematic therein] in dimethylformamide ("DMF," 8 mL). The solution was stirred at room temperature under an atmosphere of N$_2$ for 15 minutes, to which was added a solution of CH₃—(OCH₂CH₂)₃Br (320 mg, 1.41 mmole) in DMF (1 mL). The resulting solution was then heated under N₂ in an oil bath for 2 hours.

HPLC analysis revealed that the desired product, a mixture of α- and β-6-CH₃—(OCH₂CH₂)₃—O-3-MEM-naloxol was formed in approximately 95% yield. DMF was removed by a rotary evaporation to yield a sticky white solid. The crude product was used without further purification.

6.B. Synthesis of α and β epimer mixture of 6-CH₃—(OCH₂CH₂)₃—O-naloxol (α,β-PEG₃-Nal)

The crude α- and β-6-CH₃—(OCH₂CH₂)₃—O-3-MEM-naloxol mixture from 6.A. above was dissolved in 3 mL of CH₂Cl₂ to form a cloudy solution, to which was added 4 mL of trifluoroacetic acid ("TFA"). The resulting solution was stirred at room temperature for 4 hours. HPLC analysis showed that the reaction was complete. The solvent, CH₂Cl₂, was removed by a rotary evaporation. To the remaining solution was added 5 mL of water, followed by addition of K₂CO₃ to destroy excess TFA and adjust the pH to 8. The solution was then extracted with CHCl₃ (3×50 mL). The CHCl₃ extracts were combined and extracted with 0.1 N HCl solution (3×50 mL). The remaining water phase was again adjusted to a pH of 8 by addition of K₂CO₃, followed by extraction with CHCl₃ (3×50 mL). The combined organic extracts were then dried over Na₂SO₄. Following removal of the solvents, a colorless sticky solid was obtained.

The solid was purified by passage through a silica gel column (2 cm×30 cm) twice using CHCl₃/CH₃OH (30:1) as the eluent. The purified product, a mixture of the α and β epimers of 6-CH₃—(OCH₂CH₂)₃—O-naloxol containing about equal amounts of the α and β epimers, was characterized by NMR. (46 mg, 0.097 mmole, 41% isolated yield based on 6-hydroxyl-3-MEM-O-naloxone). $^1$H NMR (δ, ppm, CDCl₃): 6.49-6.72 (2H, multiplet, aromatic proton of naloxol), 5.79 (1H, multiplet, olefinic proton of naloxol), 5.17 (2H, multiplet, olefinic protons of naloxol), 4.71 (1H, doublet, $C_5$ proton of α naloxol), 4.52 (1H, doublet, $C_5$ proton of β naloxol), 3.89 (1H, multiplet, $C_6$ proton of α naloxol), 3.56-3.80 (12H, multiplet, PEG), 3.39 (3H, singlet, methoxy protons of PEG, α epimer), 3.38 (3H, singlet, methoxy protons of PEG, β epimer), 3.22 (1H, multiplet, $C_6$ proton of β naloxol), 1.14-3.12 (14H, multiplet, protons of naloxol).

6.C. Separation of α-6-CH₃—(OCH₂CH₂)₃—O-naloxol and β-6-CH₃—(OCH₂CH₂)₃—O-naloxol About 80 mg of a crude mixture of α and β epimers of PEG₃-Nal was dissolved in a minimum of CHCl₃ and loaded onto a silica gel column (2 cm×30 cm) prepared using CHCl₃. The column was carefully eluted with a CHCl₃/CH₃OH mixture (60:1). Pure α-PEG₃-Nal was the first-eluting species (26 mg, 33% isolated yield), followed by pure β-PEG₃-Nal (30 mg, 38% isolated yield). Both compounds were colorless sticky solids. α-PEG₃-Nal, $^1$H NMR (δ, ppm, CDCl₃): 6.49-6.73 (2H, two doublet, aromatic proton of naloxol), 5.79 (1H, multiplet, olefinic proton of naloxol), 5.17 (2H, triplet, olefinic protons of naloxol), 4.71 (1H, doublet, $C_5$ proton of naloxol), 3.81 (1H, multiplet, $C_6$ proton of naloxol), 3.57-3.80 (12H, multiplet, PEG), 3.40 (3H, singlet, methoxy protons of PEG), 1.13-3.12 (14H, multiplet, protons of naloxone). β-PEG₃-Nal, $^1$H NMR (δ, ppm, CDCl₃): 6.54-6.72 (2H, two doublet, aromatic proton of naloxol), 5.77 (1H, multiplet, olefinic proton of naloxol), 5.15 (2H, triplet, olefinic protons of naloxol), 4.51 (1H, doublet, $C_5$ proton of naloxol), 3.58-3.78 (12H, multiplet, PEG), 3.39 (3H, singlet, methoxy protons of PEG), 3.20 (1H, multiplet, $C_6$ proton of naloxol), 1.30-3.12 (13H, multiplet, protons of naloxol).

α,β-6-CH₃—(OCH₂CH₂)₅—O-naloxol ("α,β-PEG₅-Nal") and α,β-6-CH₃—(OCH₂CH₂)₇—O-naloxol ("α,β-PEG₇-Nal") were similarly prepared, and their individual isomers separated and isolated.

Example 7

Oral Bioavailability of PEG-Mers of Cis-Retinoic Acid and Naloxol

Female Sprague Dawley® rats (150-200 g) were obtained from Harlan Labs. They were cannulated in the external jugular vein and allowed at least 72 hours of acclimatization before the start of the study. The animals were fasted overnight (day −1), but water was provided ad libitum.

On the morning of dosing (day 0), each rat was weighed and the cannulas flushed with heparin (1000 U/mL). With the aid of a feeding tube, the animals were then dosed orally (gavage) with aqueous formulations containing either the PEGylated or the free drug. The dose was determined on a mg/kg body weight basis. The total volume of the dose did not exceed 10 mL/kg. At specific time intervals (1, 2 and 4 hours), blood samples (approximately 1.0 mL) were removed through the cannula, placed in 1.5 mL centrifuge tubes containing 14 µL of heparin, mixed and centrifuged to separate the plasma. The plasma samples were frozen (<−70° C.) until assayed. The plasma samples were purified by a precipitation technique and the analyte extracted and assayed using a high performance liquid chromatography (LC) method with a mass selective detector (MSD). Standard samples were prepared in the same way to create a standard curve, from which the concentration of unknown samples could be extrapolated (see results in Table II). When appropriate, an internal standard was used in the analysis.

Selected properties of the tested compounds (such as the molecular weight and solubility) are summarized in Table I. The in-vitro enzyme binding activity of some of the tested compounds are also reported as $IC_{50}$ values in Table 1

TABLE 1

Selected Properties of Tested Compounds

| Drug | Molecular Weight | Solubility (µM) | $IC_{50}$ (nM)* |
|---|---|---|---|
| 13-cis-Retinoic Acid (parent drug) | 300.45 | 0.47 | — |
| PEG₃-13-cis-RA | 445.64 | 3.13 | — |
| PEG₅-13-cis-RA | 549.45 | soluble | — |
| PEG₇-13-cis-RA | 621.45 | 58.3 | — |
| PEG₁₁-13-cis-RA | 797.45 | soluble | — |
| Naloxone "Nal" (parent drug) | 327.37 | soluble as HCl salt | 6.8 |
| α isomer of PEG₃-Nal | 475.6 | soluble | 7.3 |
| β isomer of PEG₃-Nal | 475.6 | soluble | 31.7 |
| α isomer of PEG₅-Nal | 563.0 | soluble | 31.5 |
| β isomer of PEG₅-Nal | 563.0 | soluble | 43.3 |
| α isomer of PEG₇-Nal | 652.0 | soluble | 40.6 |
| β isomer of PEG₇-Nal | 652.0 | soluble | 93.9 |
| α isomer of PEG₉-Nal | 740.0 | soluble | 64.4 |
| β isomer of PEG₉-Nal | 740.0 | soluble | 205.0 |
| Hydroxyzine "Hyd" (parent drug) | 374.91 | soluble as HCl salt | 48.8 |
| PEG₁-Hyd | 433.0 | soluble | 70.3 |
| PEG₃-Hyd | 521.0 | soluble | 105.0 |
| PEG₅-Hyd | 609.0 | soluble | 76.7 |
| Cetirizine "Cet" (parent drug) | 388.89 | soluble as HCl salt | 77.1 |
| PEG₁-Cet | 446.0 | soluble | 61.0 |

TABLE 1-continued

Selected Properties of Tested Compounds

| Drug | Molecular Weight | Solubility (µM) | $IC_{50}$ (nM)* |
|---|---|---|---|
| $PEG_3$-Cet | 534.0 | soluble | 86.4 |
| $PEG_5$-Cet | 622.0 | soluble | 128.0 |

*Mu-opiate binding activity for naloxone series of compounds Histamine H-1 binding activity for hydroxyzine and cetirizine series of compounds The oral bioavailabilities of the retinoic acid series of compounds were calculated and the results provided in Table II. All the data was normalized to a 6 mg/kg dose. The plasma concentration versus time profiles for these compounds are provided in FIG. 1.

TABLE II

Oral Bioavailabilities of the Retinoic Acid Series of Compounds

| Drug | Mean Plasma Concentration (ng/mL) ± SD | | N (rats) |
|---|---|---|---|
| | 1 hr | 2 hr | |
| 13-cis-Retinoic Acid | 43.3 ± 24.0 | 23.3 ± 14.8 | 3 |
| $PEG_3$-13-cis-RA | 131.8 ± 55.0 | 158.0 ± 133.0 | 7 |
| $PEG_5$-13-cis-RA | 77.7 ± 31.6 | 61.6 ± 57.1 | 4 |
| $PEG_7$-13-cis-RA | 44.0 ± 13.0 | 38.7 ± 4.2 | 3 |
| $PEG_{11}$-13-cis-RA | 21.8 ± 7.1 | 58.2 ± 43.5 | 4 |

Figure 2:
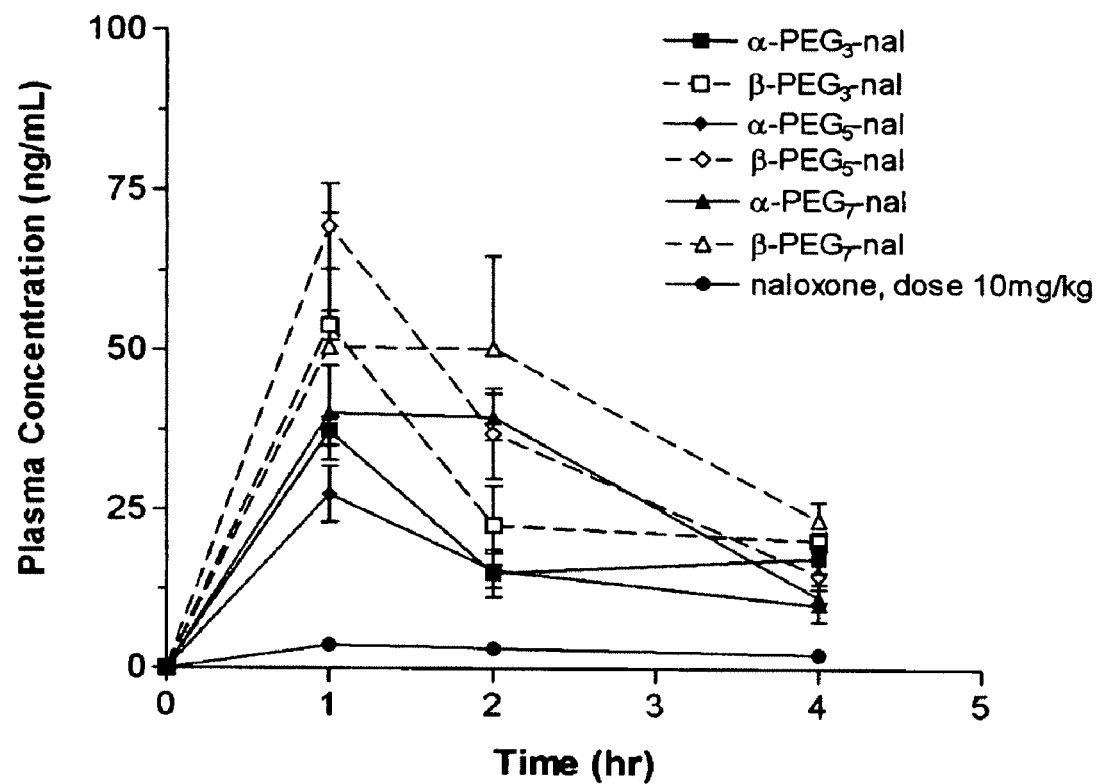
FIG. 2 is a plot of plasma concentration versus time for 6-naloxol and exemplary small PEG conjugates thereof (3-mer, 5-mer, 7-mer) administered to Sprague Dawley rats as described in detail in Example 7.

The oral bioavailability of each isomer in the naloxone series of compounds was calculated and is provided in Table III. The oral naloxone dose was either 5 or 10 mg/kg and the doses for the PEGylated compounds were normalized to 1 mg/kg dose. The plasma concentration versus time profiles for these compounds is provided in FIG. 2.

TABLE III

Oral Bioavailabilities of the Naloxone Series of Compounds

| Drug | Mean Plasma Concentration (ng/mL) ± SD | | N (rats) |
|---|---|---|---|
| | 1 hr | 2 hr | |
| Naloxone | 3.67 ± 1.05 | 3.11 ± 0.46 | 4 |
| α-$PEG_3$-Nal | 37.28 ± 4.99 | 14.92 ± 5.27 | 5 |
| β-$PEG_3$-Nal | 53.79 ± 5.19 | 22.47 ± 8.78 | 5 |
| α-$PEG_5$-Nal | 27.37 ± 10.82 | 15.38 ± 6.65 | 6 |
| β-$PEG_5$-Nal | 69.34 ± 15.03 | 36.92 ± 15.84 | 5 |
| α-$PEG_7$-Nal | 40.08 ± 16.61 | 39.51 ± 9.57 | 4 |
| β-$PEG_7$-Nal | 50.41 ± 36.44 | 50.08 ± 25.28 | 4 |

The above results show that PEGylation of small, lipophilic compounds like retinoic acid and naloxone (the free base form) increases their solubility and oral bioavailability. On the other hand, attachment of oligomeric PEGs also increases the molecular weight of the parent compound (greater than about 500 Daltons), which in turn can restrict the oral permeation of highly water soluble compounds, particularly with increasing PEG-mer length, as seen for example with $PEG_7$-13-cis-RA and $PEG_{11}$-13-cis-RA.

Example 8

Transport Across the Blood Brain Barrier (BBB) of PEG-Mers of Cis-Retinoic Acid and Naloxone As utilized for these experiments, the in situ brain perfusion technique employed the intact rat brain to (i) determine drug permeation across the BBB under normal physiological conditions, and (ii) to study transport mechanisms such as passive diffusion verses carrier mediated transport.

Perfusion was performed using the single time-point method. Briefly, the perfusion fluid (perfusate) containing the test compound(s) was infused into rats via the left external carotid artery at a constant rate by an infusion pump (20 mL/min). Perfusion flow rate was set to completely take over fluid flow to the brain at normal physiologic pressure (80-120 mm Hg). The duration of the perfusion was 30 seconds. Immediately following the perfusion, the brain vasculature was perfused for an additional 30 seconds with drug-free perfusate to remove residual drug. The pump was turned off and the brain was then immediately removed from the skull. Left-brain samples from each rat were first weighed and then homogenized using a Polytron homogenizer. Four (4) mL of 20% methanol was added to each rat brain for homogenization. After homogenization, the total volume of homogenate was measured and recorded.

A measured amount of the homogenate was diluted with organic solvent and subsequently centrifuged. The supernatant was removed, evaporated in a stream of nitrogen and reconstituted and analyzed by LC/MS/MS. Quantification of drug concentrations in brain homogenate was performed against calibration curves generated by spiking the drugs into blank (i.e. drug-free) brain homogenate. Analysis of the drug concentrations in brain homogenates was carried out in triplicate, and the values were used to calculate the brain uptake rate in pmole per gram of rat brain per second of perfusion.

Each perfusion solution contained atenolol (target concentration, 50 µM), antipyrine (target concentration, 5 µM) and a test compound (13-cis-retinoic acid, $PEG_n$-13-cis-retinoic acid, naloxone or $PEG_n$-Nal) at a target concentration of 20 µM.

The BBB uptake of each compound tested was calculated, normalized and recorded in Table IV. All the data was normalized to a 5 µM dosing solution at 20 mL/min perfusion rate for 30 sec.

TABLE IV

Blood-Brain Barrier (BBB) Uptake for Tested Compounds

| Drug | Normalized Brain Uptake Rate in pmole/gm brain/sec (Mean ± SD) | N (rats) |
|---|---|---|
| Atenolol (low standard) | 0.7 ± 0.9 | 4 |
| Antipyrine (high standard) | 17.4 ± 5.7 | 4 |
| 13-cis-Retinoic Acid | 102.54 ± 37.31 | 4 |
| $PEG_3$-13-cis-RA | 79.65 ± 20.91 | 4 |
| $PEG_5$-13-cis-RA | 58.49 ± 13.44 | 3 |
| $PEG_7$-13-cis-RA | 24.15 ± 1.49 | 3 |
| $PEG_{11}$-13-cis-RA | 17.77 ± 1.68 | 3 |
| Naloxone | 15.64 ± 3.54 | 3 |
| $PEG_3$-Nal | 4.67 ± 3.57 | 3 |
| $PEG_5$-Nal | 0.96 ± 0.36 | 3 |
| $PEG_7$-Nal (α isomer) | 0.94 ± 0.32 | 3 |
| $PEG_7$-Nal (β isomer) | 0.70 ± 0.19 | 3 |
| Hydroxyzine | 355.89 ± 59.02 | 3 |
| $PEG_5$-Hyd | 131.60 ± 15.84 | 3 |
| $PEG_7$-Hyd | 12.01 ± 2.97 | 3 |
| Cetrizine | 1.37 ± 0.37 | 3 |
| $PEG_5$-Cet | 4.32 ± 0.26 | 3 |
| $PEG_7$-Cet | 1.13 ± 0.05 | 3 |

The above results demonstrate that PEGylation of a lipophilic compound such as 13-cis-retinoic acid can significantly reduce its brain uptake rate ("BUR"), e.g., by a factor of four in the case of $PEG_7$-13-cis-RA, and by a factor of five in the case of $PEG_{11}$-13-cis-RA as compared to the parent compound "13-cis-retinoic acid". In the case of naloxone, a reduction in BUR of 16 times was observed for PEG$_5$-Nal and PEG$_7$-Nal. With respect to hydroxyzine, the BUR was reduced about 29 times when administered as PEG$_7$-Hyd. The relatively minimal transport of cetirizine across the blood-brain barrier was not altered significantly when administered as PEG$_7$-Cet.

Thus, overall, it was surprisingly discovered that by attaching small water-soluble polymers to small molecule drugs such as these, one can optimize a drug's delivery profile by modifying its ability to cross biological membranes, such as the membranes associated with the gastro-intestinal barrier, the blood-brain barrier, the placental barrier, and the like. More importantly, it was discovered that, in the case of orally administered drugs, attachment of one or more small water-soluble polymers is effective to significantly reduce the rate of transport of such drugs across a biological barrier such as the blood-brain barrier. Ideally, the transport of such modified drugs through the gastro-intestinal tract is not adversely impacted to a significant degree, such that while transport across the biological barrier such as the blood-brain barrier is significantly impeded, the oral bioavailability of the modified drug is retained at a clinically effective level.

Figure 3:
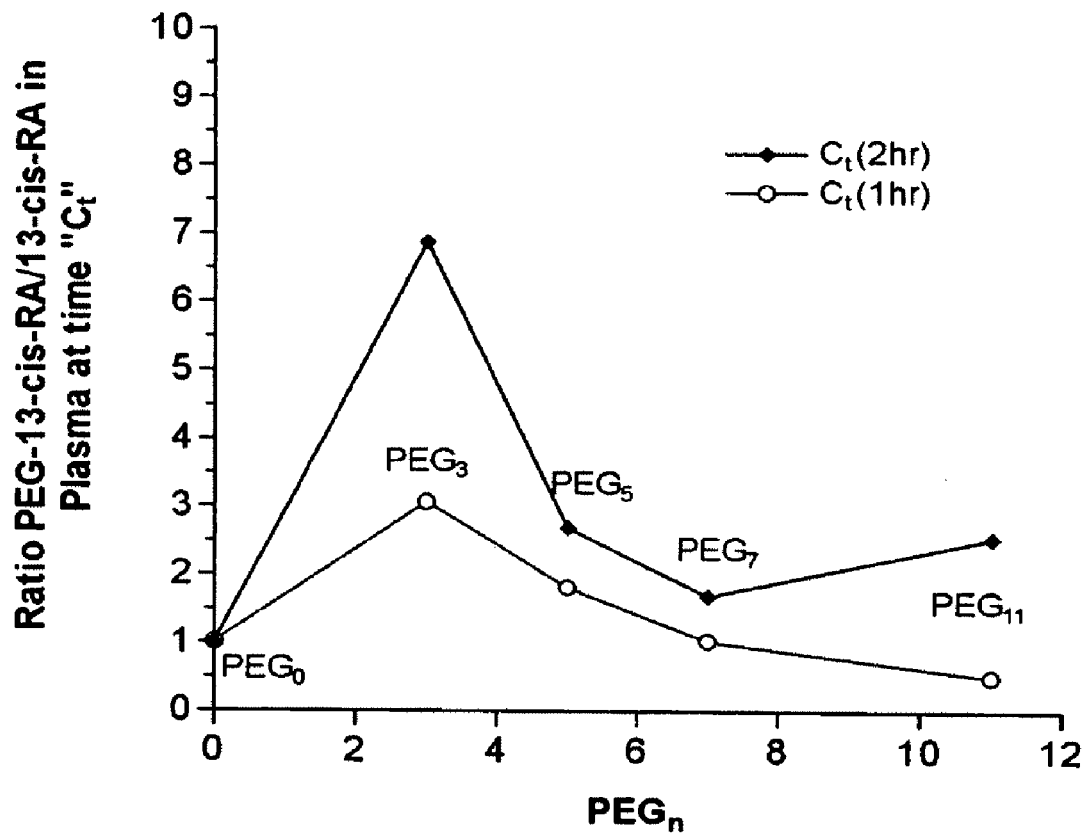
FIG. 3 is a plot demonstrating the effect PEG chain length on the intestinal transport (as an indicator of oral bioavailability) of various PEG-13-cis-RA conjugates and 13-cis-RA in Sprague-Dawley rats.
Figure 4:
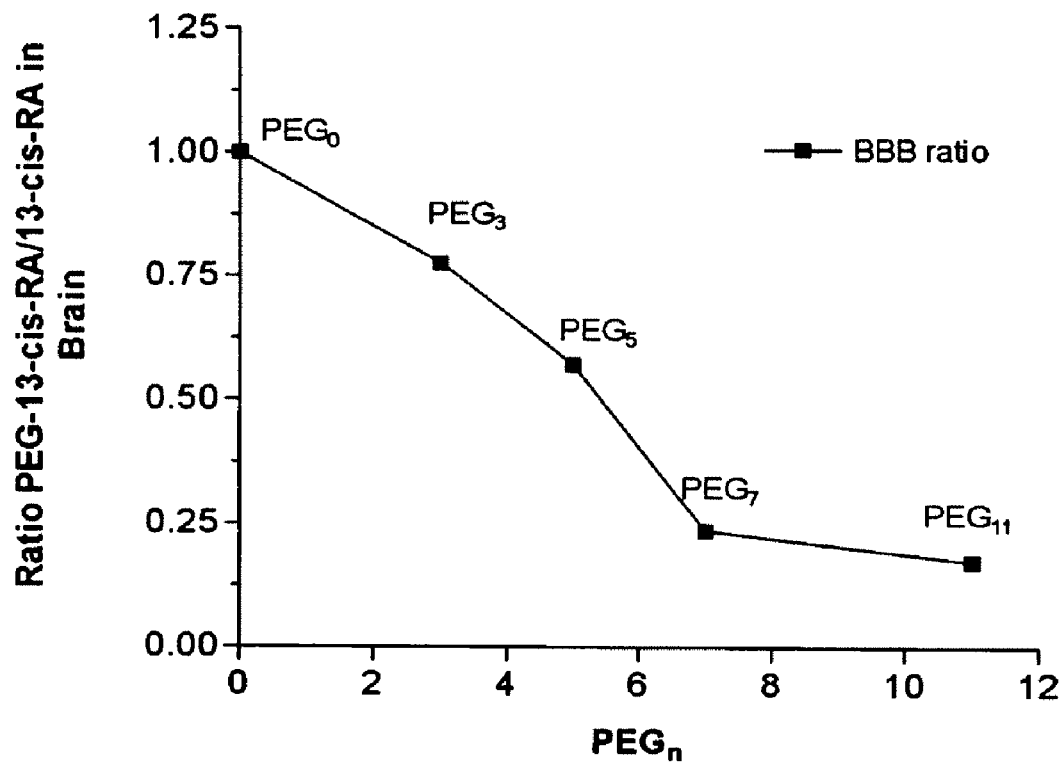
FIG. 4 is a plot demonstrating the effect of covalent attachment of various sized PEG-mers on the blood-brain barrier transport of 13-cis-RA and various PEG-13-cis-RA conjugates.
Figure 5:
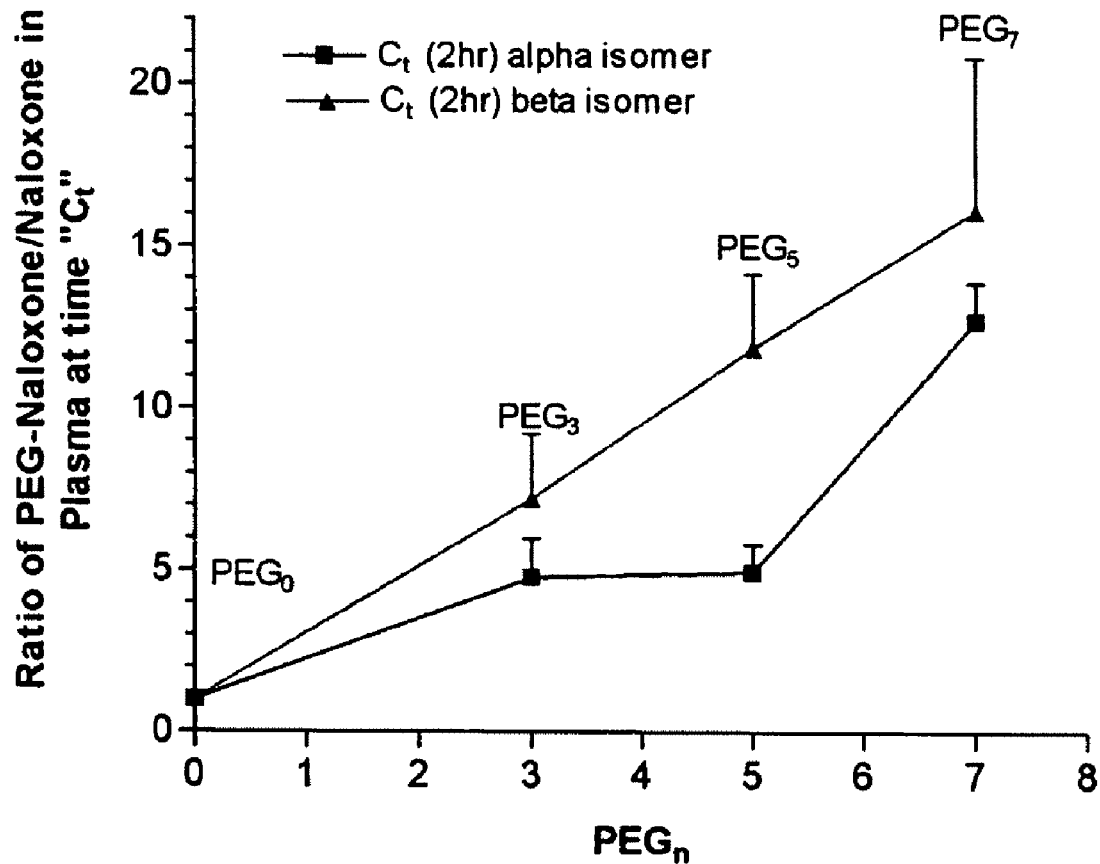
FIG. 5 is a plot demonstrating the effect of covalent attachment of various sized PEG-mers on the intestinal transport (as an indicator of oral bioavailability) of naloxone and $PEG_n$-Nal.
Figure 6:
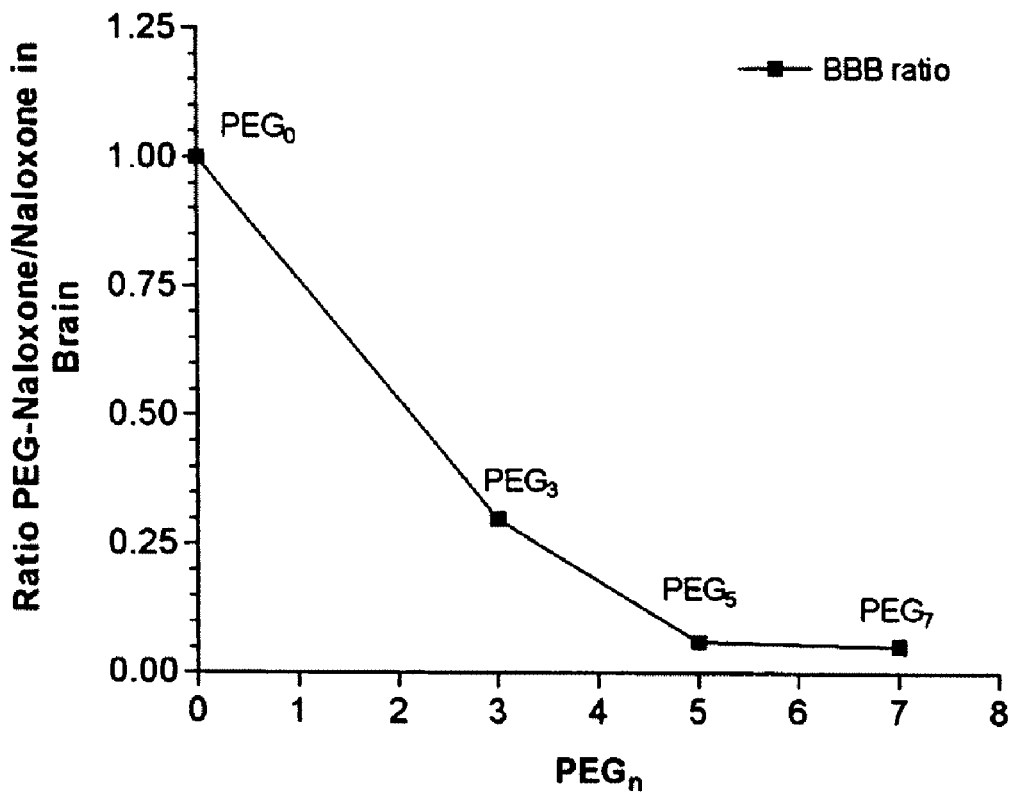
FIG. 6 is a plot showing the effect of covalent attachment of various sized PEG-mers on the blood-brain barrier transport of naloxone and $PEG_n$-Nal.
Figure 7:
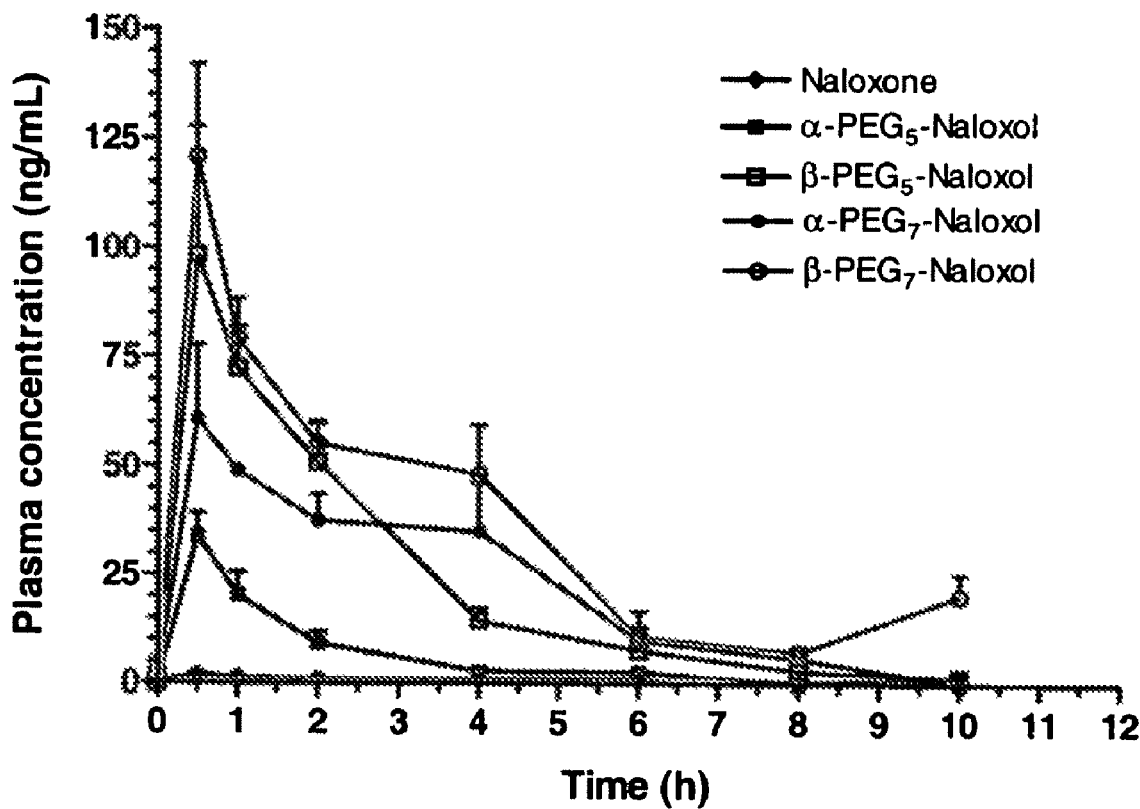
FIG. 7 is a plot demonstrating the pharmacokinetics of naloxone and $PEG_n$-Nal in rats following oral gavage.

The data generated in Examples 7 and 8 was plotted in order to compare the effect of PEG size on the relative oral bioavailability and BBB transport of 13-cis-retinoic acid and naloxone, respectively. See FIGS. 3-7. In FIG. 3, the effect of attaching each of a PEG 3-mer, a PEG 5-mer, a PEG 7-mer and a PEG 11-mer to 13-cis-retinoic acid on its oral bioavailability is examined. In FIG. 4, the effect of covalent attachment of these various PEG-mers on the blood-brain barrier transport of 13-cis-retinoic acid is examined. In FIG. 5, the effect of covalent attachment of each a PEG 3-mer, PEG 5-mer and a PEG 7-mer on the oral bioavailability of naloxone is examined. FIG. 6 demonstrates the effect of covalent attachment of such PEG-mers on the blood brain-barrier transport of naloxone. FIG. 7 shows that the PEG$_n$-Nal compounds had a higher oral bioavailability than naloxone. As can be seen from these figures, as the size of the PEG oligomer increases, the BBB uptake rate significantly decreases, while the oral bioavailability increases relative to that of the parent molecule.

The difference in oral bioavailability between the α- and β-isomers of naloxone may be due to the differences in their physicochemical properties. One isomer appears to be slightly more lipophilic than the other isomer, and thereby results in a small difference in oral bioavailability.

Example 9

In-Vitro Metabolism of PEG-Naloxol

An in vitro method was developed to study the effect of PEGylation on the Phase II metabolism (glucuronidation) of naloxone. The procedure calls for the preparation of a NADPH regenerating system (NRS) solution. The NRS solution is prepared by dissolving sodium bicarboante (22.5 mg) in 1 mL of deionized water. Into this solution B-nicotinamide adenine dinucleotide phosphate sodium salt or NADP (1.6 mg), glucose-6-phosphate (7.85 mg), glucose-6-phosphate dehydrogenase (3 μL), uridine 5-diphosphoglucuronic acid trisodium salt or UDPGA (2.17 mg), adenosine 3'-phosphate 5'-phosphosulfate lithium salt or PAPS (0.52 mg), and 1 M magnesium chloride solution (10 μL) were added. After the solids were all dissolved, the solution was stored in an ice bath.

30 mM test article stock solutions were prepared by dissolving weighed amounts of naloxone HCl, 6-mPEG$_3$-O-Naloxone, α-6-mPEG$_5$-O-naloxone, and α-mPEG$_7$-O-Naloxone in 1 mL of deionized water.

Male Sprague Dawley rat microsomes (0.5 mL at 20 mg/mL concentration; M00001 from In-vitro Technologies, Baltimore, Md.) were removed from the freezer and thawed in an ice bath. Forty μL of the liver microsomes were diluted to 100 μL with 60 μL of deionized water in a test vial. To the test vial, tris buffer, pH 7.4 (640 μL) and a test article stock (10 μL) were added to have 750 μL volume.

Each test vial and the NRS solution were separately placed in a 37° C. water bath for 5 minutes. The NRS solution (250 μL) was added into each test vial. The reaction timer was started at the addition of the NRS to the first test vial. Each sample (200 μL) was collected and then perchloric acid (20 μL) was added to terminate the reaction. The samples were collected at the following time points: 0-2, 20, 40 and 60 minutes. All of the terminated test vials were stored in an ice bath.

Acetonitrile (100 μL) was added into each test vial, which was then centrifuged at 3000×g for 5 minutes. Supernatant (230 μL) was withdrawn and then 10 μL of the test solution was assayed by an LC/MS method. The concentration of test article in each sample was measured and recorded at each time point.

Table V lists the percentage of active remaining after incubation with liver microsomes.

TABLE V

Percentage of Active Remaining After Incubation with Liver Microsomes

| Time (min) | naloxone | α-PEG$_3$-Nal | β-PEG$_3$-Nal | α-PEG$_5$-Nal | α-PEG$_7$-Nal |
|---|---|---|---|---|---|
| 0 | 100.0 | 100.0 | 100.0 | 100.0 | 100.0 |
| 20 | 47.1 | 64.8 | 83.9 | 84.1 | 87.4 |
| 40 | 27.6 | 51.7 | 75.2 | 75.6 | 81.6 |
| 60 | 15.6 | 45.7 | 69.6 | 69.2 | 76.9 |

In view of the results in Table V, it is possible to conclude that PEGylation with an oligomer decreases that rate of glucuronidation for a small molecule such as naloxol. Furthermore, as the PEG oligomer chain increases, the rate of glucuronidation decreases. In addition, comparison of α-isomers and β-isomers of PEG$_3$-naloxol, shows that the β-isomer is a poor substrate for cytochrome P450 isozymes in the isolated rat liver microsomes. This observation confirms the in-vivo data illustrated in FIG. 7.

Figure 8:
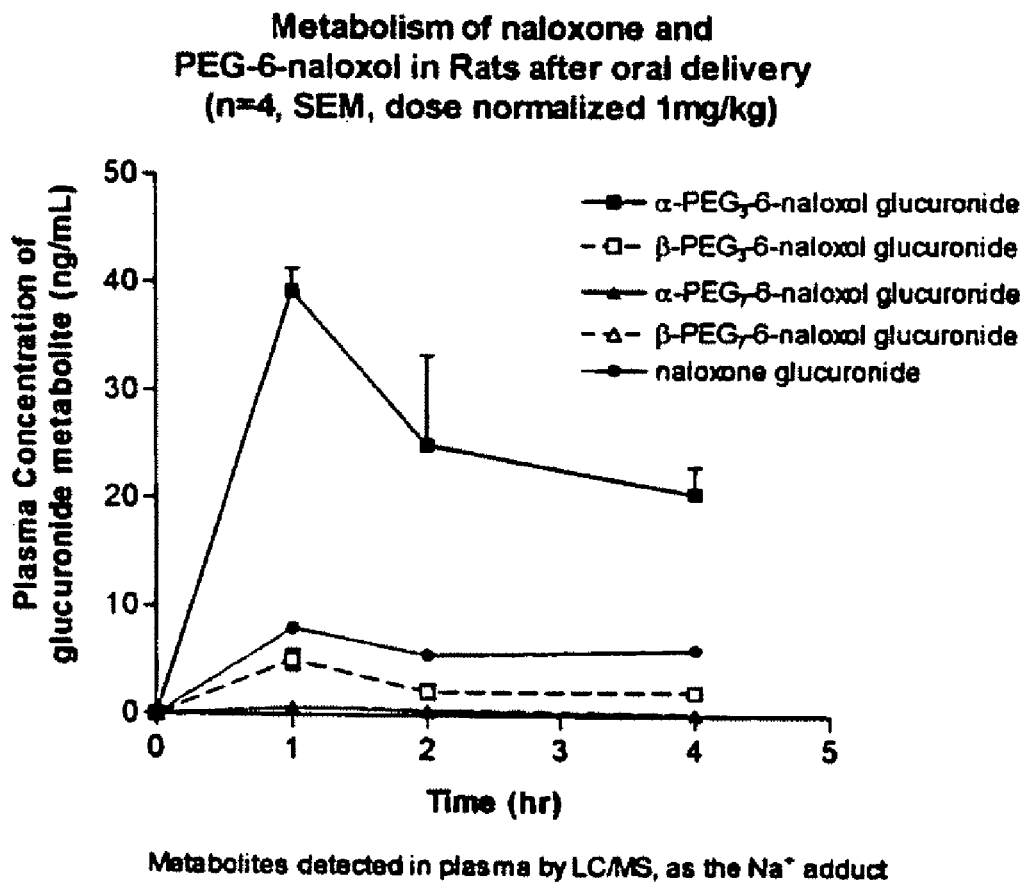
FIG. 8 and FIG. 9 are plots demonstrating the effect of covalent attachment of various sized PEG-mers on the level of naloxone metabolites and $PEG_n$-Nal metabolites.
Figure 9:
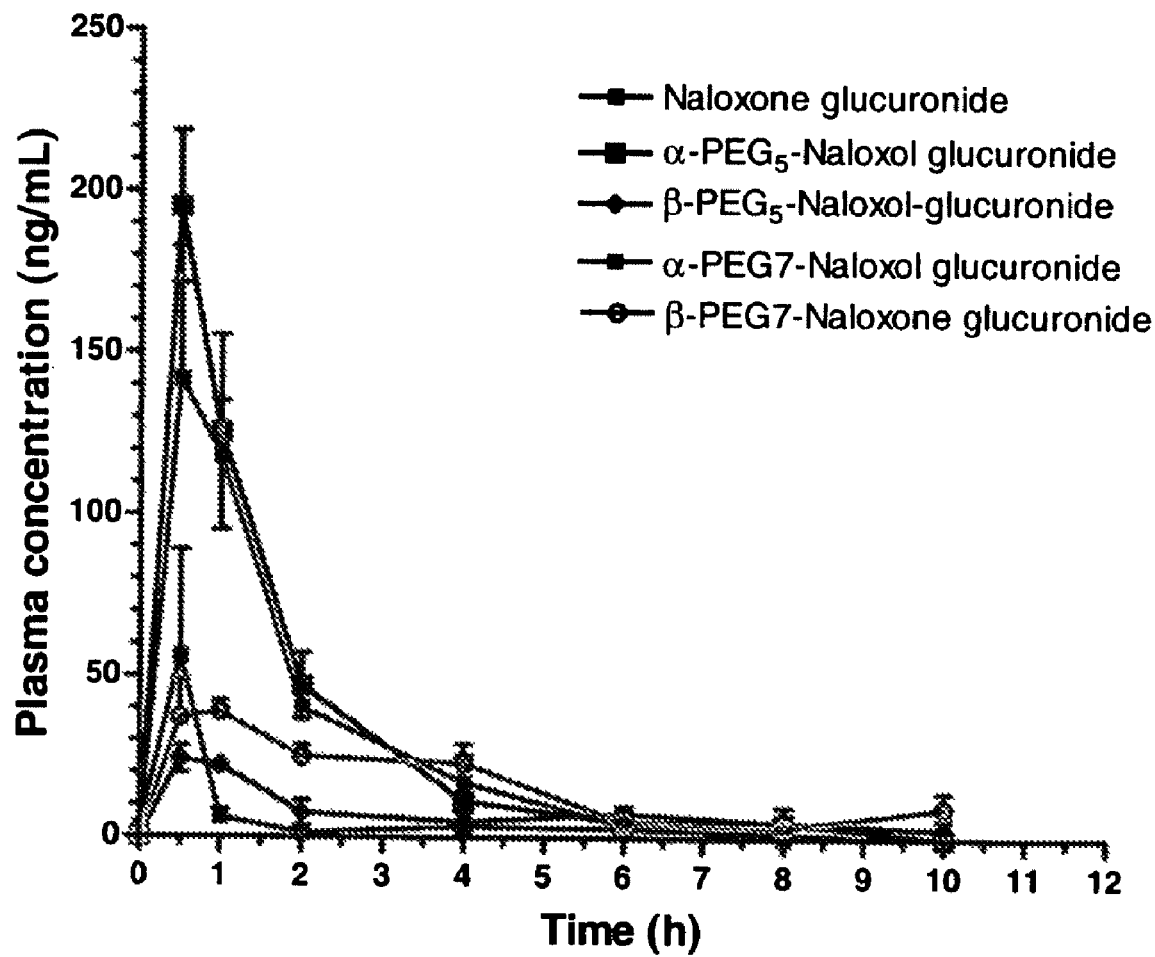

Turning to the data in FIGS. 8 and 9, it appears that attachment of small PEGs can be effective in decreasing the rate of drug metabolism (as indicated by glucuronide formation in the case of naloxone). The higher levels of the β-isomer in the blood when compared to the α-isomer is likely due to a significant prevention of the first pass effect, that is to say, a significant prevention of the extent of first pass metabolism (FIG. 7), resulting from covalent attachment of the oligomeric PEG molecule. The PEG molecule may create steric hinderance and/or hydrophilic or hydrophobic effects, which when the PEG is attached to the β-isomer form, alters the affinity of the β-isomer conjugate to cytochrome P450 isozymes to a greater degree than when the PEG is attached to the α-isomer form. The levels of β-isomer metabolite are lower when compared to the α-isomer metabolite and unPEGylated naloxone.

Example 10

Activity of Various Opiod Antagonist on μ-Opiate Receptors

In a separate series of experiments, the bioactivity of naloxone, other opiod antagonists, and various conjugates on n-opiate receptors was determined in-vitro. The results are summarized in Table VI.

TABLE VI

Activity of Naloxone and PEG$_n$-6-Naloxol Conjugates on μ-Opiate Receptors, in-vitro.

| Compound | Molecular Weight | EC$_{50}$ (nM) |
| --- | --- | --- |
| Naloxone | 327.4 | 6.8 |
| 3-PEG$_3$-O-naloxone | 474 | 2910.0 |
| 6-NH$_2$-naloxone | 601 | 29.2 |
| PEG$_{550}$-6-NH-naloxone (PEG$_{13}$ amide) | 951 | 210.0 |
| α-6-naloxol | 329 | 2.0 |
| β-6-naloxol | 329 | 10.8 |
| α-PEG$_3$-Nal | 475.6 | 7.3 |
| β-PEG$_3$-Nal | 475.6 | 31.7 |
| α-PEG$_5$-Nal | 563 | 31.5 |
| β-PEG$_5$-Nal | 563 | 43.3 |
| α-PEG$_7$-Nal | 652 | 40.6 |
| β-PEG$_7$-Nal | 652 | 93.9 |

In the table above, for each compound, the bioactivity is provided as a measure of the relative bioactivity of each of the various PEG conjugates in comparison to parent drug. The EC$_{50}$ is the concentration of agonist that provokes a response halfway between the baseline and maximum response in a standard dose-response curve. As can be seen from the above data, each of the PEG$_n$-Nal conjugates is bioactive, and in fact, all of the 6-naloxone or naloxol conjugates maintained a degree of bioactivity that is at least 5% or greater than that of the parent drug, with bioactivities ranging from about 5% to about 35% of the bioactivity of the unmodified parent compound. In terms of bioactivity, PEG$_{550}$-6-NH-naloxone possesses about 13% of the bioactivity of the parent compound (6-NH$_2$-naloxone), α-PEG$_3$-Nal possesses about 30% of the bioactivity of the parent compound (α-6-OH-naloxol), and β-PEG$_5$-Nal possesses about 35% of the bioactivity of the parent compound (α-6-OH-naloxol).

Example 11

Method of Making Substantially Unimolecular Weight Oligo(Ethylene Glycol) Methyl Esters and their Derivatives The unimolecular (monodisperse) PEGs of the present invention were prepared as set forth in detail below. These unimolecular PEGs were particularly advantageous in providing the modified active agents of the present invention, and in imparting the desired modification of barrier transport properties of the subject active agents.

The method exemplified below represents another aspect of the present invention, that is, a method for preparing monodisperse oligo(ethylene oxide) methyl ethers from low molecular weight monodisperse oligo(ethylene glycol)s using halo-derivatized (e.g., bromo derivatized) oligo(ethylene oxide). Also provided herein, in another aspect of the invention, is a method of coupling oligo(ethylene oxide) methyl ether (from a unimolecular weight composition) to an active agent using a halo-derivatized oligo(ethylene oxide) methyl ether.

Schematically, the reaction can be represented as follows:

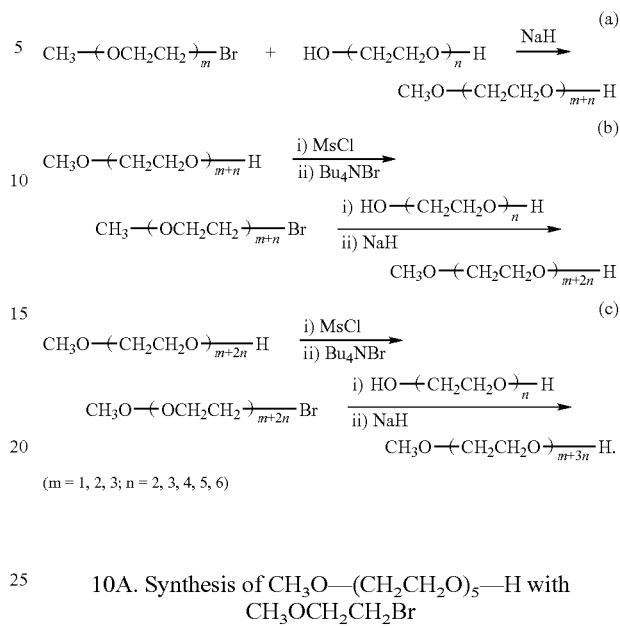

(m = 1, 2, 3; n = 2, 3, 4, 5, 6)

10A. Synthesis of CH$_3$O—(CH$_2$CH$_2$O)$_5$—H with CH$_3$OCH$_2$CH$_2$Br

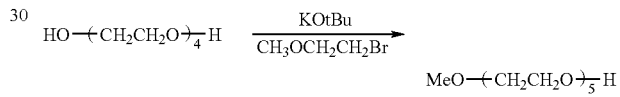

Tetra(ethylene glycol) (55 mmol, 10.7 g) was dissolved in 100 mL of tetrahydrofuran ("THF") and to this solution was added KOtBu (55 mL, 1.0M in THF) at room temperature. The resulting solution was stirred at room temperature for 30 minutes, followed by dropwise addition of CH$_3$OCH$_2$CH$_2$Br (55 mmol, 5.17 mL in 50 mL THF). The reaction was stirred at room temperature overnight, followed by extraction with H$_2$O (300 mL)/CH$_2$Cl$_2$ (3×300 mL). The organic extracts were combined and then dried over anhydrous Na$_2$SO$_4$. After filtering off the solid drying agent and removing the solvent by evaporation, the recovered crude residue was purified by column chromatography using a silica gel column (CH$_2$Cl$_2$:CH$_3$OH=60:1~40:1) to give pure penta(ethylene glycol) monomethyl ether (yield 35%). $^1$H NMR (CDCl$_3$) δ 3.75-3.42 (m, 20H, OCH$_2$CH$_2$O), 3.39 (s, 3H, MeO).

10.B. Synthesis of CH$_3$O—(CH$_2$CH$_2$O)$_7$—H Using MeOCH$_2$CH$_2$Br

To a solution of hexa(ethylene glycol) (10 g, 35 mmole) and 2-bromoethyl methyl ether (4.9 g, 35 mmole) in THF (100 mL) was slowly added sodium hydride (2.55 g, 106 mmole). The solution was stirred at room temperature for two hours. HPLC indicated that mPEG$_7$-OH was formed in about 54% yield. The reaction was then stopped by the addition of diluted hydrochloride acid to destroy excess sodium hydride. All solvents were removed using a rotary evaporator to give a brown sticky liquid. Pure mPEG$_7$-OH was obtained as a colorless liquid (4.9 g, 41% isolated yield) by using semi-preparative HPLC (20 cm×4 cm, C18 column, acetonitrile and water as mobile phases). $^1$H NMR (CDCl$_3$): 2.57 ppm (triplet, 1H, OH); 3.38 ppm (singlet, 3H, CH$_3$O); 3.62 ppm (multiplet, 30H, OCH$_2$CH$_2$).

10.C. Synthesis of CH₃O—(CH₂CH₂O)₅—Br

Triethyl amine (5.7 ml, 40 mmol) was added to CH₃O—(CH₂CH₂O)₅—OH (5.0 g, 20 mmol) with stirring. The solution was cooled in an ice bath under N₂, and 2.5 ml of methanesulfonyl chloride (32 mmol) was added dropwise over 30 minutes. The solution was then stirred overnight at room temperature. Water (40 ml) was added to the reaction mixture and the solution was extracted with CH₂Cl₂ (3×150 ml) and the organic phase was washed with 0.1 N HCl (3×80 ml) and water (2×80 ml). After drying with Na₂SO₄ and removal of solvent, a light brown liquid was obtained. The product and Bu₄NBr (12.80 g, 39.7 mmol) were dissolved in CH₃CN (50 ml), and the resulting solution was stirred under N₂ at 50° C. for 15 hours. After cooling to room temperature, CH₃CN was removed by rotary evaporation to give a red liquid, which was dissolved in 150 ml water and extracted with EtOAc (2×200 ml). The organic phase was combined, washed with water, and dried over Na₂SO₄. After the removal of solvent, a red liquid was obtained (4.83 g, 77.4%). ¹H NMR (300 Hz, CDCl₃): δ 3.82 (t, 2H), 3.67 (m, 14H), 3.51 (m, 2H), 3.40 (s, 3H).

Example 11

Synthesis of mPEG3 N-Mefloquine

To a methanol solution (5 mL) of mefloquine HCl salt (200 mg, 0.48 mmol) and mPEG₃-Butyaldehyde (280 mg, 1.20 mmol) was added sodium cyanoborohydride (60 mg, 0.96 mmol) water solution (1 mL). The resulting solution was heated under nitrogen with stirring in an oil bath at 50° C. for 16 hours. HPLC showed that the reaction was complete. All solvents were then removed by a rotary evaporator to give a crude product. After purified by a preparative reverse phase HPLC, pure mPEG-3-N-Mefloquine conjugate was obtained as a colorless sticky liquid (160 mg, 0.27 mmol, 56% isolated yield). ¹H NMR (CDCl₃, ppm): 8.15 (multiplet, 3H, aromatic ring); 7.73 (triplet, 1H, aromatic ring); 5.86 (doublet, 1H, CH); 3.67 (multiplet, 14H, PEG back bone); 3.52 (singlet, 3H, PEG-OCH₃); 3.18 (multiplet, 2H, PEG-CH₂); 0.52-2.74 (multiplet, 13H, PEG and cyclohexyl protons).

Schematically, the reaction can depicted as follows:

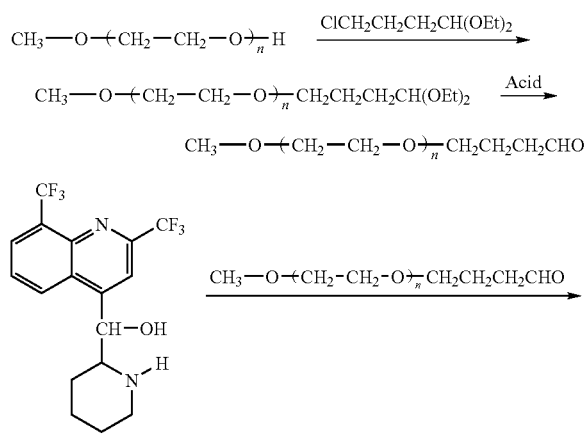

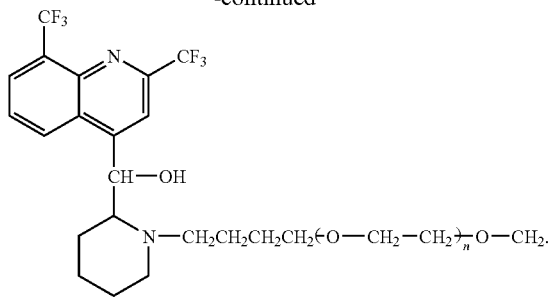

What is claimed is:

1. A compound selected from the group consisting of:
    6-CH₃-(OCH₂CH₂)₅-O-naloxol;
    6-CH₃-(OCH₂CH₂)₆-O-naloxol;
    6-CH₃-(OCH₂CH₂)₈-O-naloxol; and
    6-CH₃-(OCH₂CH₂)₉-O-naloxol;
or a pharmaceutically acceptable salt thereof, wherein the compound is an α-6 isomer, a β-6 isomer or a mixture of α-6 and β-6 isomers.

2. The compound of claim 1, wherein the compound is selected from the group consisting of
    α,β-6-CH₃-(OCH₂CH₂)₅-O-naloxol;
    α,β-6-CH₃-(OCH₂CH₂)₆-O-naloxol;
    α,β-6-CH₃-(OCH₂CH₂)₈-O-naloxol; and
    α,β-6-CH₃-(OCH₂CH₂)₉-O-naloxol;
or a pharmaceutically acceptable salt thereof.

3. The compound of claim 2, wherein the compound is α,β-6-CH₃-(OCH₂CH₂)₅-O-naloxol or a pharmaceutically acceptable salt thereof.

4. The compound of claim 2, wherein the compound is α,β-6-CH₃-(OCH₂CH₂)₆-O-naloxol or a pharmaceutically acceptable salt thereof.

5. The compound of claim 2, wherein the compound is α,β-6-CH₃-(OCH₂CH₂)₈-O-naloxol or a pharmaceutically acceptable salt thereof.

6. The compound of claim 2, wherein the compound is α,β-6-CH₃-(OCH₂CH₂)₉-O-naloxol or a pharmaceutically acceptable salt thereof.

7. The compound of claim 1, wherein the compound is selected from the group consisting of
    α-6-CH₃-(OCH₂CH₂)₅-O-naloxol;
    α-6-CH₃-(OCH₂CH₂)₆-O-naloxol;
    α-6-CH₃-(OCH₂CH₂)₈-O-naloxol; and
    α-6-CH₃-(OCH₂CH₂)₉-O-naloxol;
or a pharmaceutically acceptable salt thereof.

8. The compound of claim 7, wherein the compound is α-6-CH₃-(OCH₂CH₂)₅-O-naloxol or a pharmaceutically acceptable salt thereof.

9. The compound of claim 7, wherein the compound is α-6-CH₃-(OCH₂CH₂)₆-O-naloxol or a pharmaceutically acceptable salt thereof.

10. The compound of claim 7, wherein the compound is α-6-CH₃-(OCH₂CH₂)₈-O-naloxol or a pharmaceutically acceptable salt thereof.

11. The compound of claim 7, wherein the compound is α-6-CH₃-(OCH₂CH₂)₉-O-naloxol or a pharmaceutically acceptable salt thereof.

12. The compound of claim 1, wherein the compound is selected from the group consisting of
    β-6-CH₃-(OCH₂CH₂)₅-O-naloxol;
    β-6-CH₃-(OCH₂CH₂)₆-O-naloxol;
    β-6-CH₃-(OCH₂CH₂)₈-O-naloxol; and
    β-6-CH₃-(OCH₂CH₂)₉-O-naloxol;
or a pharmaceutically acceptable salt thereof.

13. The compound of claim 12, wherein the compound is β-6-CH$_3$-(OCH$_2$CH$_2$)$_5$-O-naloxol or a pharmaceutically acceptable salt thereof.

14. The compound of claim 12, wherein the compound is β-6-CH$_3$-(OCH$_2$CH$_2$)$_6$-O-naloxol or a pharmaceutically acceptable salt thereof.

15. The compound of claim 12, wherein the compound is β-6-CH$_3$-(OCH$_2$CH$_2$)$_8$-O-naloxol or a pharmaceutically acceptable salt thereof.

16. The compound of claim 12, wherein the compound is β-6-CH$_3$-(OCH$_2$CH$_2$)$_9$-O-naloxol or a pharmaceutically acceptable salt thereof.

17. A pharmaceutical composition comprising a compound of any one of claims 1-16 or a pharmaceutically acceptable salt thereof, and a pharmaceutically acceptable excipient.

* * * * *